US008038983B2

(12) United States Patent
McBride et al.

(10) Patent No.: US 8,038,983 B2
(45) Date of Patent: Oct. 18, 2011

(54) FLUORINATED CARBOHYDRATE CONJUGATES

(75) Inventors: William J. McBride, Boonton, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 998 days.

(21) Appl. No.: 10/901,441

(22) Filed: Jul. 29, 2004

(65) Prior Publication Data

US 2005/0136001 A1    Jun. 23, 2005

Related U.S. Application Data

(60) Provisional application No. 60/490,884, filed on Jul. 29, 2003.

(51) Int. Cl.
*A61K 51/00* (2006.01)
*A61M 36/14* (2006.01)
(52) U.S. Cl. ...................... 424/1.65; 424/1.89
(58) Field of Classification Search .................. 424/1.89
See application file for complete search history.

(56) References Cited

U.S. PATENT DOCUMENTS

| | | | |
|---|---|---|---|
| 3,471,329 A * | 10/1969 | Nitsch et al. ................. 127/46.2 |
| 3,927,193 A | 12/1975 | Hansen et al. |
| 4,150,149 A | 4/1979 | Wolfsen et al. |
| 4,160,675 A * | 7/1979 | Pannekeet et al. ........... 127/46.2 |
| 4,331,647 A | 5/1982 | Goldenberg |
| 4,348,376 A | 9/1982 | Goldenberg |
| 4,361,544 A | 11/1982 | Goldenberg |
| 4,361,644 A | 11/1982 | Urban et al. |
| 4,444,744 A | 4/1984 | Goldenberg |
| 4,460,459 A | 7/1984 | Shaw et al. |
| 4,460,561 A | 7/1984 | Goldenberg |
| 4,468,457 A | 8/1984 | Goldenberg et al. |
| 4,624,846 A | 11/1986 | Goldenberg |
| 4,735,210 A | 4/1988 | Goldenberg |
| 4,818,709 A | 4/1989 | Primus et al. |
| 4,932,412 A | 6/1990 | Goldenberg |
| 5,019,368 A | 5/1991 | Epstein et al. |
| 5,091,542 A | 2/1992 | Ahlem et al. |
| 5,101,827 A | 4/1992 | Goldenberg |
| 5,128,119 A | 7/1992 | Griffiths |
| 5,262,524 A | 11/1993 | Anderson et al. |
| 5,308,944 A * | 5/1994 | Stone-Elander et al. ..... 219/687 |
| 5,328,679 A | 7/1994 | Hansen et al. |
| 5,332,567 A | 7/1994 | Goldenberg |
| 5,435,990 A * | 7/1995 | Cheng et al. ................. 424/1.53 |
| 5,525,338 A | 6/1996 | Goldenberg |
| 5,633,425 A | 5/1997 | Lonberg et al. |
| 5,635,603 A * | 6/1997 | Hansen et al. ............. 530/391.5 |
| 5,697,902 A | 12/1997 | Goldenberg |
| 5,716,595 A | 2/1998 | Goldenberg |
| 5,736,119 A | 4/1998 | Goldenberg |
| 5,746,996 A | 5/1998 | Govindan et al. |
| 5,753,206 A | 5/1998 | McBride et al. |
| 5,767,285 A * | 6/1998 | Hamann et al. ................ 548/542 |
| 5,772,981 A | 6/1998 | Govindan et al. |
| 5,776,093 A | 7/1998 | Goldenberg |
| 5,776,094 A | 7/1998 | Goldenberg |
| 5,776,095 A | 7/1998 | Goldenberg |
| 5,808,020 A * | 9/1998 | Ferrieri et al. ................ 536/18.5 |
| 5,827,690 A | 10/1998 | Meade et al. |
| 5,837,242 A | 11/1998 | Holliger et al. |
| 5,851,527 A | 12/1998 | Hansen |
| 5,874,540 A | 2/1999 | Hansen et al. |
| 5,882,626 A | 3/1999 | Epstein et al. |
| 5,892,020 A | 4/1999 | Mezes et al. |
| 5,904,915 A * | 5/1999 | Fujibayashi et al. ......... 424/1.73 |
| 5,922,302 A | 7/1999 | Goldenberg et al. |
| 5,932,178 A * | 8/1999 | Yamazaki et al. ............ 422/159 |
| 5,965,132 A | 10/1999 | Thorpe et al. |
| 6,004,554 A | 12/1999 | Thorpe et al. |
| 6,010,680 A | 1/2000 | Govindan et al. |
| 6,017,514 A | 1/2000 | Epstein et al. |
| 6,025,165 A | 2/2000 | Whitlow et al. |
| 6,071,491 A | 6/2000 | Epstein et al. |
| 6,077,499 A | 6/2000 | Griffiths et al. |
| 6,096,289 A | 8/2000 | Goldenberg |
| 6,126,916 A | 10/2000 | McBride et al. |
| 6,342,221 B1 | 1/2002 | Thorpe et al. |
| 6,387,350 B2 | 5/2002 | Goldenberg |
| 6,962,813 B2 * | 11/2005 | Pier et al. ...................... 435/326 |
| 7,098,302 B2 * | 8/2006 | Krag et al. .................... 530/300 |

FOREIGN PATENT DOCUMENTS

| | | |
|---|---|---|
| EP | 0 167 103 | 6/1985 |
| EP | 1034797 A2 | 9/2000 |
| WO | 03/059397 A2 | 7/2003 |
| WO | WO 03078454 A2 * | 9/2003 |
| WO | 03/086475 A1 | 10/2003 |
| WO | 2005/028490 A1 | 3/2005 |

OTHER PUBLICATIONS

Patt et al. (Applied Radiat.Isotopes 2002, 57, 705-712).*
Cervigni et al. (Angew. Chem. Int. Ed. Engl. 1996, 35, 1230-1232).*
King et al. (Biochemistry 1986, 25, 5774-5779).*
Karacay et al. (Bioconj. Chem. 2000, 11, 842-854).*
Andreana et al., *Org. Lett.*, 4(11):1864 (2002).
Arcamone, *Cancer Res.*, 45:5995 (1985).
Bakina et al., *J. Med. Chem.*, 40:4013 (1997).
Barbas et al., *Methods: A Companion to Methods in Enzymology*, 2:119 (1991).
Bei et al., *J. Immunol. Meth.*, 186:245 (1995).
Beuthien-Baumann et al., *Carbohydrate Res.*, 327:107 (2000).
Carter et al., *Proc. Nat'l Acad. Sci. USA*, 89:4285 (1992).
Colman, *Biochem. Soc. Symp.*, 63:141, 1998.
Coloma et al., *Nat. Biotech.*, 15:159 (1997).
Courtenay-Luck et al., "Genetic Manipulation of Monoclonal Antibodies", *Monoclonal Antibodies: Production, Engineering, and Clinical Application*, pp. 166-179, Ritter (eds.), Cambridge University Press (1995).

(Continued)

Primary Examiner — Michael G Hartley
Assistant Examiner — Melissa Perreira
(74) Attorney, Agent, or Firm — Richard A. Nakashima

(57) ABSTRACT

Disclosed are novel conjugates that include fluorinated carbohydrate molecules and methods for synthesizing the conjugates. The fluorinated carbohydrate molecule may include a radioisotope. The method of synthesizing the conjugate is useful for labeling selected molecules, and the conjugates may be useful in diagnostic or therapeutic methods. Particularly, the conjugates may be useful in diagnostic or therapeutic kits.

1 Claim, 15 Drawing Sheets

OTHER PUBLICATIONS

Fiedler et al., *Biotechnol.*, 13:1090 (1995).
Fiedler et al., *Immunotechnol.*, 3:205 (1997).
FitzGerald et al., *Protein Eng.*, 10(10):1221 (1997).
Hande et al., *Cancer Res.*, 48:1829 (1988).
Hasan et al., *Prog. Clin. Biol. Res.*, 288:471 (1989).
Jackson et al., *Brit. J. Cancer Res.*, 78(2):181 (1998).
Jones et al., *Nature*, 321:522 (1986).
Kaneko et al., *Bioconjug. Chem.*, 2(3):133 (1991).
Kostik et al., *J. Org. Chem.*, 66:2618 (2001).
Larrick et al., *Methods: A Companion to Methods in Enzymol.*, 2(2):106 (1991).
Mack et al., *Proc. Natl. Acad. Sci. USA*, 92:7021 (1995).
Mahiouz et al., *J. Immunol. Meth.*, 212:149 (1998).
Mendez et al., *Nat. Genet.*, 15:146 (1997).
Mew et al., *J. Immunol.*, 130:1473 (1983).
Mew et al., *Cancer Res.*, 45:4380 (1985).
Miller et al., *Ann. Rev. Microbiol.*, 42:177 (1988).
Orlandi et al., *Proc. Nat'l Acad. Sci. USA*, 86:3833 (1989).
Osbourn et al., *Immunotechnol.*, 2:181 (1996).
Oseroff et al., *Proc. Nat'l Acad. Sci USA*, 83:8744 (1986).
Oseroff et al., *Photochem. Photobiol.*, 46:83 (1987).
Papanikos et al., *J. Am. Chem. Soc.*, 123:2176 (2001).
Patt et al., *App. Radiat. Isotopes*, 57:705 (2002).
Pèlegrin et al., *Cancer*, 67:2529 (1991).
Potter et al., *Cancer Res.*, 58:2646 (1998).
Ridder et al., *Bio/Technol.*, 13:255 (1995).
Riechmann et al., *Nature*, 332:323 (1988).
Rodriguez et al., *J. Org. Chem.*, 63:7134 (1998).
Sandhu, *Crit. Rev. Biotech.*, 12:437 (1992).
Tarli et al., *Blood*, 94(1):192 (1999).
Tatsuta et al., *Lasers Surg. Med.*, 9:422 (1989).
Tomizuka et al., *Nature Genet.*, 16:133 (1997).
van den Bergh, *Chem. Britain*, 22:430 (1986).
Vaughan et al., *Nature Biotech.*, 14:309 (1996).
Verhoeyen et al., *Science*, 239:1534 (1988).
Wang et al., *Cancer Res.*, 52:4484 (1992).
Wang et al., *Proc. Natl. Acad. Sci USA*, 100(1):56 (2003).
Ward et al., "Genetic Manipulation and Expression of Antibodies", *Monoclonal Antibodies: Principles and Applications*, pp. 137-185 (1995).
Wester et al., *Eur. J. Nucl. Med. Molec. Imag.*, 30(1):117 (2003).
Winter et al., *Ann. Rev. Immunol.*, 12:433 (1994).
Yang et al., *Appl. Environ. Microbiol.*, 64(8):2869 (1998).
Yu et al., *Int. J. Cancer*, 56:244 (1994).
Zhu et al., *Bio/Technol.*, 14:192 (1996).
Zhu et al., *J. Org. Chem.*, 68:5641 (2003).
Barthel et al., "3'-deoxy-3'-[18F]fluorothymidine as a new marker for monitoring tumor response to antiproliferative therapy in vivo with positron emission tomography", Cancer Res. Jul. 1, 2003;63(13):3791-8.
Haubner et al., "Noninvasive imaging of alpha(v)beta3 integrin expression using 18F-labeled RGD-containing glycopeptide and positron emission tomography", Cancer Res. Mar. 1, 2001;61(5):1781-5.
Sorger et al., "[18F]Fluoroazomycinarabinofuranoside (18FAZA) and [18F]Fluoromisonidazole (18FMISO): a comparative study of their selective uptake in hypoxic cells and PET imaging in experimental rat tumors", Nucl Med Biol. Apr. 2003;30(3):317-26.
Supplementary European Search Report for EP 04821595.8 completed Aug. 19, 2010.

* cited by examiner

IMP 278 + Cold FDG 30 Min

IMP 278 + Cold FDG After 1 hr 40 min

IMP 278 + Cold FDG After 20 min at 50°C

FLUORINATED CARBOHYDRATE CONJUGATES

This application claims priority to U.S. Provisional Application Ser. No. 60/490,884, filed Jul. 29, 2003, the contents of which are hereby incorporated by reference in their entirety.

BACKGROUND

Many diagnostic methods such as radioimmunodetection ("RAID"), positron-emission tomography ("PET"), and magnetic resonance imaging ("MRI"), and therapeutic methods, such as radioimmunotherapy ("RAIT"), require the use of small labeled molecules. $^{18}$F, (i.e., "F-18"), a positron emitter having a half-life of approximately 2 hours and an energy of 0.65 MeV, is a desirable radioisotope for labeling small molecules used in many of the aforementioned methods. However, normally it is a time consuming complicated process to elucidate a method of incorporating short-lived isotopes such as F-18 into small molecules useful for diagnostic or therapeutic use. Therefore, a method of easily incorporating F-18 into small molecules is desirable. An F-18 derivative of 2-Deoxy-D-Glucose, (e.g., F-18, 2-Fluoro-2-Deoxy-D-Glucose, wherein the fluorine atom on the C2 carbon is F-18) is widely produced and can be a useful molecule for labeling small molecules by producing F-18 carbohydrate conjugates or adducts.

SUMMARY

Disclosed herein is a conjugate or adduct comprising a fluorinated carbohydrate molecule linked to a second molecule. The conjugate is useful in diagnostic or therapeutic methods, for example, methods that require small labeled molecules. As such, the fluorinated carbohydrate molecule typically includes an isotope of fluorine (e.g., F-17, F-18, F-19, F-20, and/or F-21) that can be detected in an imaging method (e.g., PET, MRI, RAID, etc.). In some claims, it may be desirable to link more than one fluorinated carbohydrate molecule to a second molecule.

In particular, the second molecule may be a carrier or a targeting molecule, and/or the second molecule may be selected such that the conjugate is useful as a carrier or as a targeting molecule. The second molecule may include an amino acid, peptides, antibodies, or antibody fragments. Bi-specific or multispecific antibodies may be selected as second molecules.

The fluorinated carbohydrate molecule may include a variety of monosaccharides and/or their enantiomers including glucose, mannose, galactose, talose, gulose, idose, altrose, allose, ribose, arabinose, xylose, lyxose, erythrose, threose, and/or glyceraldehyde. The fluorinated carbohydrate molecule also may include ketose sugars (e.g., psicose, fructose, sorbose, and/or tagatose), disaccharides, (e.g., lactose, maltose, and/or sucrose), and/or polysaccharides.

A particularly suitable fluorinated carbohydrate molecule for forming the conjugate or adduct may include 2-Fluoro-2-Deoxy-D-Glucose or "FDG" (and preferably F-18, 2-Fluoro-2-Deoxy-D-Glucose). Fluorinated (e.g., F-18) derivatives of the FDG precursor (e.g., 1,3,4,6,-tetra-O-Acetyl-2-O-trifluoromethanesulfonyl-β-D-mannopyranose or mannose triflate) are also suitable fluorinated carbohydrate molecules. The fluorinated carbohydrate molecule may be linked to the second molecule by any suitable linkage, for example, a hydrazone linkage, hydrazine linkage, an amide linkage, an amino linkage, an imino linkage, an oxime linkage, a sulfide linkage, a thiosemicarbazone linkage, a semicarbazone, a carbon—carbon bond (e.g., formed through an ylide reaction), or a boronic acid linkage. The hemiacetal of FDG may be used to form the FDG conjugate.

Also disclosed is a simple, convenient method of introducing isotopes of fluorine onto a second molecule. Generally, the method involves using a fluorinated carbohydrate derivative to introduce fluorine onto a second molecule (e.g., a carrier or a targeting molecule). Readily available FDG (e.g., F-18, FDG) can be used as a reactive intermediate to introduce fluorine isotopes onto targeting molecules such as peptides or antibodies. The active functional groups on the FDG, (e.g., the alcohols and/or the aldehyde) can be used to link the carbohydrate to the molecules of interest. Classes of molecules that can be labeled in this manner may include antibodies, bi-specific antibodies, fragments of antibodies, peptides, amino acids, and any other molecule where labeling with an isotope is desirable. In particular, this method can be used to attach F-18, FDG to a molecule such as a peptide or protein, which can ultimately be identified using PET. The method can also be used to attach F-19, FDG to a second molecule, which can ultimately be identified using MRI.

In one claim, a hydrazine moiety on a carrier, such as an aryl-hydrazine moiety, can be used to form a hydrazone bond with the aldehyde portion of the fluorinated carbohydrate molecule (e.g., FDG), in order to form a hydrazone linkage. The hydrazine linkage may be reduced with a reducing agent to form a substituted hydrazine linkage.

In another claim, the aldehyde group on a fluorinated carbohydrate molecule, (e.g., FDG), can form an imine bond with an amino group on a second molecule in order to form an amino linkage. For instance, the imino bond can be reduced in-situ to form a stable amino linkage. Other possible linkages include an amide linkage, a sulfide linkage, a semicarbazone linkage, a thiosemicarbazone linkage, an oxime linkage, and a carbon—carbon bond (e.g., formed through an ylide reaction), and/or a boronic acid linkage.

Alternatively, nucleophilic derivatives of the fluorinated carbohydrate molecule may also be created that can subsequently be reacted with groups on the second molecule. For example, derivatives of FDG that contain aminooxy, hydrazide, or thiosemicarbazide groups at their reducing termini (i.e., at their aldehyde group) may be created. These derivatives may be reacted with second molecules, for example at a carbonyl carbon, to create oxime, hydrazone, or thiosemicarbazone linkages.

A wide variety of second molecules (e.g., carriers and/or targeting molecules) are suitable for the described method, provided that the second molecule and the fluorinated carbohydrate molecule can be linked. For example, a carrier may be an amino acid or a peptide molecule. For peptides, the fluorinated carbohydrate may be linked to one or more suitable amino acids present within the peptide. As such, the peptide molecule may contain reactive groups (e.g., aldehyde, or keto groups).

The peptide molecule may be designed to function as a targeting molecule, in which the molecule can be targeted to a site of interest by receptor targeting, antibody pretargeting, or other receptor targeting agents. The peptide may include haptens and/or chelators. Where the peptide molecule comprises chelators, the chelators may be complexed with metal ions, and the metal ions may include radioisotopes. Suitable peptides may include by example (reading from amino to carboxy end): (1) H$_2$N—NH—CH$_2$—CO-Lys(X)-Tyr-Lys(X)—NH$_2$ ; (2) O═CH—CO-Lys(X)-Tyr-Lys(X)—NH$_2$ ; (3) H$_2$N—NH—C$_6$H$_4$—CO-Lys(X)-Tyr-Lys(X)—NH$_2$ ; (4) Ac-Cys-Lys(X)-Tyr-Lys(X)NH$_2$ (SEQ ID NO: 1); (5) Gly-Lys(X)-Tyr-Lys(X)—NH$_2$ (SEQ ID NO: 2); (6) H$_2$N—NH—

CS—NH—C$_6$H$_4$—CO-D-Lys(X)-D-Glu-D-Lys(X)—NH$_2$; (7) H$_2$N—NH—CS—NH—C$_6$H$_4$—CO-Lys(X)-Tyr-Lys(X)—NH$_2$; and/or (8) H$_2$N—O—CH$_2$—CO-Lys(X)-Tyr-Lys(X)—NH$_2$; wherein X is an antigenic molecule, a hapten, a hard acid chelator, and/or a soft acid chelator.

In particular, the conjugate may comprise an antibody molecule or antibody fragment linked to the fluorinated carbohydrate molecule. For certain methods, it may be desirable to link the fluorinated carbohydrate molecule to an antibody that is multispecific (e.g., a bi-specific antibody) and/or multivalent, and as such provide a labeled antibody. The same chemistry used to label peptides can be used to label antibodies (such as multispecific antibodies) or fragments of antibodies. The fluorinated carbohydrate molecule and antibody or antibody fragment may be linked by several different types of linkages, for example, a hydrazone linkage or a hydrazine linkage, an amino linkage or an imino linkage, an amide linkage, a sulfide linkage, a thiosemicarbazone linkage, a semicarbazone linkage, an oxime linkage, a carbon—carbon bond (e.g., formed through an ylide reaction), and/or a boronic acid linkage.

In one method, the conjugate may be prepared by reacting a fluorinated carbohydrate molecule with a carrier to link the fluorinated carbohydrate molecule to the carrier. For example, the conjugate may be prepared by reacting F-18, 2-Fluoro-2-Deoxy-D-Glucose with a carrier that includes a hydrazine group.

In another method for preparing the conjugate, the fluorinated carbohydrate molecule first may be converted to an aminated derivative (e.g., by reacting the fluorinated carbohydrate with ammonia, a primary or secondary amine, a hydroxyl amine or an aminooxy-containing molecule, a hydrazine, an ylide, or another nitrogen-containing molecule), and then reacted with a second molecule (e.g., a carrier containing a carbonyl carbon), to form an amide, amino, imino, hydrazone, and/or oxime linkage. For example, FDG may be reacted with an aminooxy, hydrazide, or thiosemicarbazide group to form an intermediate, which may then be reacted with a carrier to form a conjugate. The conjugate then may be reduced. Alternatively, the intermediate may be reduced prior to being reacted with a carrier, (e.g., to form an intermediate containing an oxime, hydrazone, and/or thiosemicarbazone), and the reduced intermediate may be reacted with a carrier to from the conjugate.

In another method of preparing the conjugate, one or more hydroxyl groups on the fluorinated carbohydrate molecule or a derivative of the fluorinated carbohydrate molecule may be replaced with a leaving group such as —Cl or —Br to create a further halogenated FDG derivative. Such a glucose derivative may include 1-Chloro-2-Fluoro-2-Deoxy-D-Glucose or 1-Bromo-2-Fluoro-2-Deoxy-D-Glucose, or be a part of a larger glucose derivative. For example, 1,3,4,6-tetra-O-acetyl-2-Fluoro-2-Deoxy-D-Glucose may be converted to 3,4,6-tri-O-Acetyl-1-Chloro-2-Fluoro-2-Deoxy-D-Glucose or 3,4,6-tri-O-Acetyl-1-Bromo-2-Fluoro-2-Deoxy-D-Glucose, respectively, by the method of Patt et al., *Appl. Radiat. Isot* 2002, 57, 705-712. Alternatively, the 1,3,4,6-tetra-O-acetyl-2-Fluoro-2-Deoxy-D-Glucose molecule may be treated with BF$_3$.Et$_2$O. These derivatives may then be reacted with a carrier that contains a thiol group (e.g., a thiophenol or a protein that contains a cysteine) to create a sulfide linkage. The acetyl groups of the 1,3,4,6-tetra-O-acetyl-2-Fluoro-2-Deoxy-D-Glucose derivative may be hydrolyzed after the sulfide linkage is formed.

In another method of preparation, the conjugate may be produced by reacting the fluorinated carbohydrate molecule with a carrier that contains a semicarbazide or a thiosemicarbazide group to form a semicarbazone or a thiosemicarbazone, respectively. For example, the semicarbazide or thiosemicarbazide group on a carrier may be reacted with the reducing terminus or ketone group of a fluorinated carbohydrate molecule.

In some of the claims, it may be desirable to reduce the conjugate to form a more stable linkage.

In another claim, the conjugate may be produced by using a water active ylide reaction. For example, a nitrogen ylide on a carrier or targeting molecule (such as a peptide) may be reacted with the reducing terminus or ketone group of a fluorinated carbohydrate molecule to create a carbon—carbon linkage.

The conjugate may be useful in methods of diagnosing a disease or condition that may lead to a disease. For example, a method of diagnosis may comprise (A) administering to a subject an antibody or antibody fragment having at least one arm that binds a targeted tissue and at least one other arm that binds a conjugate (i.e., targetable construct); (B) optionally, administering to the subject a clearing composition, and allowing the composition to clear non-localized antibodies or antibody fragments from circulation; and (C) administering to the subject the conjugate (i.e., targetable construct) which comprises at least one diagnostic agent, (e.g., F-18). The conjugate preferably comprises FDG and a carrier or a targeting molecule. The antibody may comprise a multispecific or bi-specific antibody. In particular, the conjugate and the antibody may be used to perform imaging methods, such as positron-emission tomography ("PET").

In another diagnostic method, it may be desirable to use the aforementioned methods to create a labeled antibody, for use with or without a targeting molecule. The labeled antibody may be used to perform imaging methods such as PET. In addition to $^{18}$F, other radionuclides that can be useful as diagnostic agents, include for example, $^{45}$Ti, $^{68}$Y, $^{111}$In, $^{124}$I, $^{131}$I, $^{99m}$Tc, $^{186}$Re, $^{188}$Re, $^{177}$Lu, $^{64}$Cu $^{67}$Cu, $^{212}$Bi, $^{213}$Bi, and/or $^{68}$Ga.

A wide variety of antibodies are suitable for the method, including a multispecific antibody (e.g., a bi-specific), and/or multivalent antibody (e.g., a trivalent antibody). One arm of the antibody may comprise a monoclonal antibody or a fragment of a monoclonal antibody that binds a targeted tissue. The other arm of the antibody may comprise a monoclonal antibody or a fragment of a monoclonal antibody that binds a conjugate. The antibody (e.g., a bi-specific antibody) may be an animal, human, chimeric or humanized antibody or comprise a fragment of an animal, human, chimeric or humanized antibody. The two arms of the antibody may be the same or different.

Where a bi-specific antibody is selected, the bi-specific antibody may comprise the Fv of Mab Mu-9 and the Fv of Mab 679, or the bi-specific antibody may comprise the Fv of anti-CEA Mab MN-14 and the Fv of Mab 679. The bi-specific antibody may also comprise a fusion protein, (e.g., a fusion protein that includes one or more of the CDRs of Mu-9, 679, and/or MN-14).

The diagnostic method may also comprise a therapeutic method. In one example, the conjugate may contain a diagnostic nuclide, such as F-18, and the antibody (or bi-specific antibody) may contain a therapeutic nuclide such as $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$SM, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{199}$Au, $^{199}$Au, and/or $^{211}$Pb.

The antibody may be designed to recognize a wide variety of natural or artificial antigens present on targeted tissue, (e.g., antigens from normal tissue, diseased tissue, pathogens, and/or haptens).

The targeted tissue may be a solid tumor such as a, a glioma, a sarcoma, and/or a carcinoma (e.g., renal, lung, intestinal, stomach, breast, ovarian, and/or prostate cancer or liver cancer). In another claim, the targeted tissue may be a multiple myeloma, a T-cell malignancy, and/or a B-cell malignancy (e.g., indolent forms of B-cell lymphomas, aggressive forms of B-cell lymphomas, chronic leukemias, acute lymphatic leukemias, multiple myeloma, and/or non-Hodgkins lymphoma).

The targeted tissue may include a tumor that produces or is associated with antigens selected from colon-specific antigen-p (CSAp), carcinoembryonic antigen (CEA), CD4, CD5, CD8, CD14, CD15, CD19, CD20, CD21, CD22, CD23, CD25, CD30, CD45, CD74, CD80, HLA-DR, Ia, Ii, MUC 1, MUC 2, MUC 3, MUC 4, NCA, EGFR, HER 2/neu, PAM-4, TAG-72, EGP-1, EGP-2, A3, KS-1, Le(y), S100, PSMA, PSA, tenascin, fibronectin (see L. Tarli et al., Blood 1999;94: 192-198), folate receptor, VEGF, placenta growth factor ("PIGF"), necrosis antigens, IL-2, IL-6, insulin-like growth factor-1 ("IGF-1"), T101, and MAGE.

The disease or condition may also include cardiovascular disease, an infectious disease (bacterial, fungal, parasitic, and/or viral), an inflammatory disease, an autoimmune disease, and/or a neurological disease.

Also disclosed is a kit useful for diagnosing diseased tissue in a subject, which includes a conjugate comprising a fluorinated carbohydrate molecule. In the kit, the conjugate typically includes a diagnostic agent, (e.g., F-18 as F-18, 2-Fluoro-2-Deoxy-D-Glucose). The conjugate may function as a targetable molecule, and as such, the conjugate typically includes at least one epitope recognizable by an antibody. The kit may also include a molecule (e.g., a bi-specific molecule or antibody) capable of binding the conjugate as a targetable molecule and/or capable of binding a selected antigen on targeted tissue. In such a kit, the molecule or antibody may include at least one arm that binds the conjugate and at least one arm that binds the selected antigen as present on a targeted tissue. The kit may also include a conjugate comprising an antibody or antibody fragment that is labeled by the aforementioned methods, for use with or without a targetable molecule. The kit may include a clearing composition useful for clearing non-localized antibodies and antibody fragments as well.

Also disclosed is a method of separating or purifying FDG or a derivative of FDG such as 1,3,4,6-tetra-O-acetyl-2-O-[$^{18}$F]-β-D-glucose. The method may include contacting a solution that includes 2-Fluoro-2-Deoxy-D-Glucose with a boronic acid resin, washing the 2-Fluoro-2-Deoxy-D-Glucose and resin; and eluting the 2-Fluoro-2-Deoxy-D-Glucose. In another claim, the method may include contacting a solution that includes 2-Fluoro-2-Deoxy-D-Glucose with a phenylhydrazine acid resin to bind excess unlabeled glucose. In another claim of the separation method, a solution that contains 1,3,4,6-tetra-O-acetyl-2-[$^{18}$F]-fluoro-2-deoxy-D-glucose and unreacted 1,3,4,6-tetra-O-acetyl-2-O-trifluoromethanesulfonyl-β-D-mannopyranose ("mannose triflate") is passed through a resin that can be alkylated to remove the excess unreacted mannose triflate, such as an activated thiol-, amino-, or a hydrazino-containing resin. The separation or purification procedure may be adapted for processes such as conventional chromatography (e.g., silica gel chromatography) or reverse phase HPLC, as well as batch purification. The separation or purification procedure may also be adapted to concentrate the F-18 labeled 2-Fluoro-2-Deoxy-D-Glucose or precursor.

DETAILED DESCRIPTION

Figure 1:
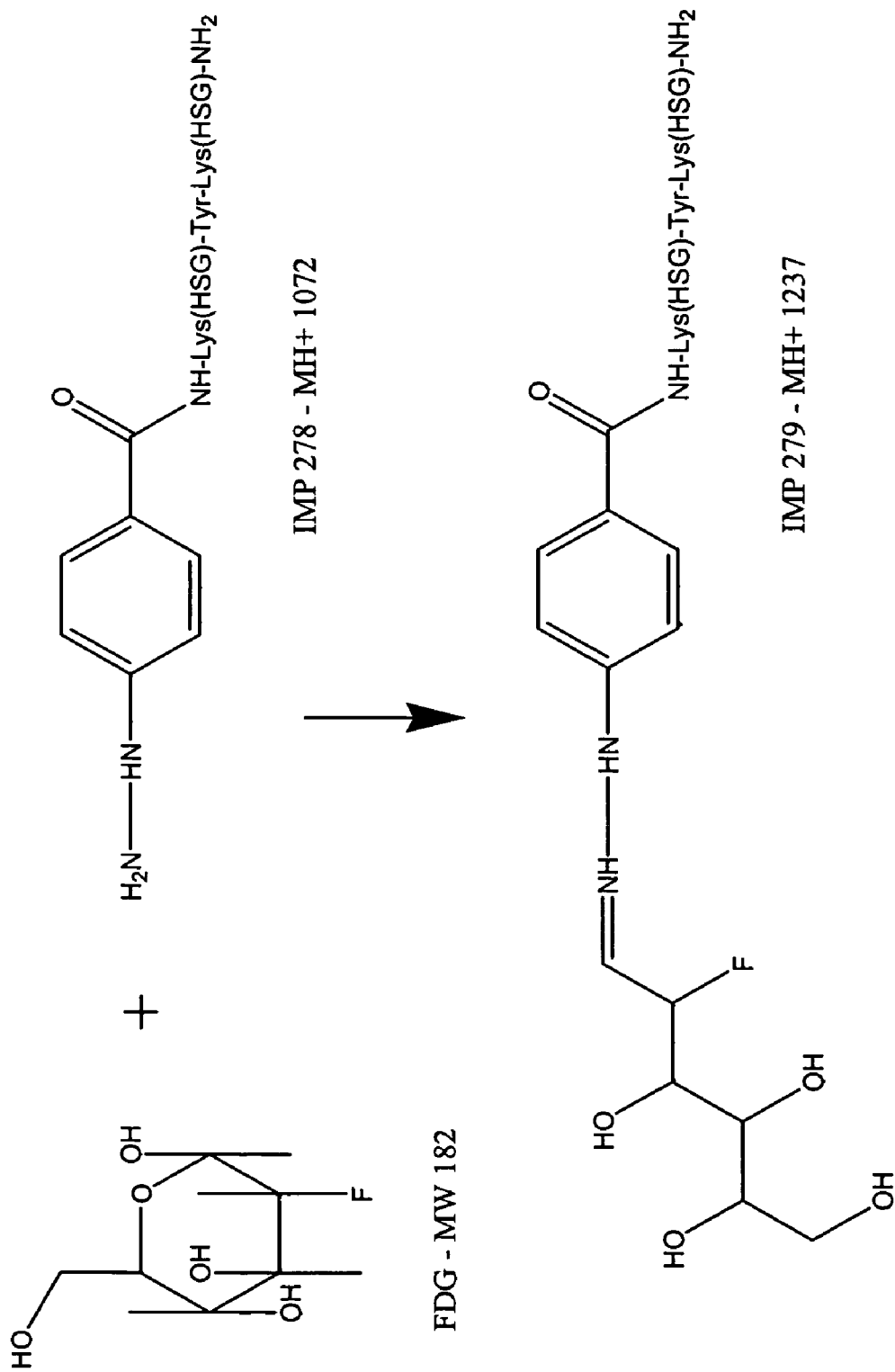
FIG. 1 is a schematic representation of the reaction of 2-Fluoro-2-Deoxy-D-Glucose with $H_2N$—NH—$C_6H_4$—CO-Lys(HSG)-Tyr-Lys(HSG)-$NH_2$ (IMP 278).
Figure 2:
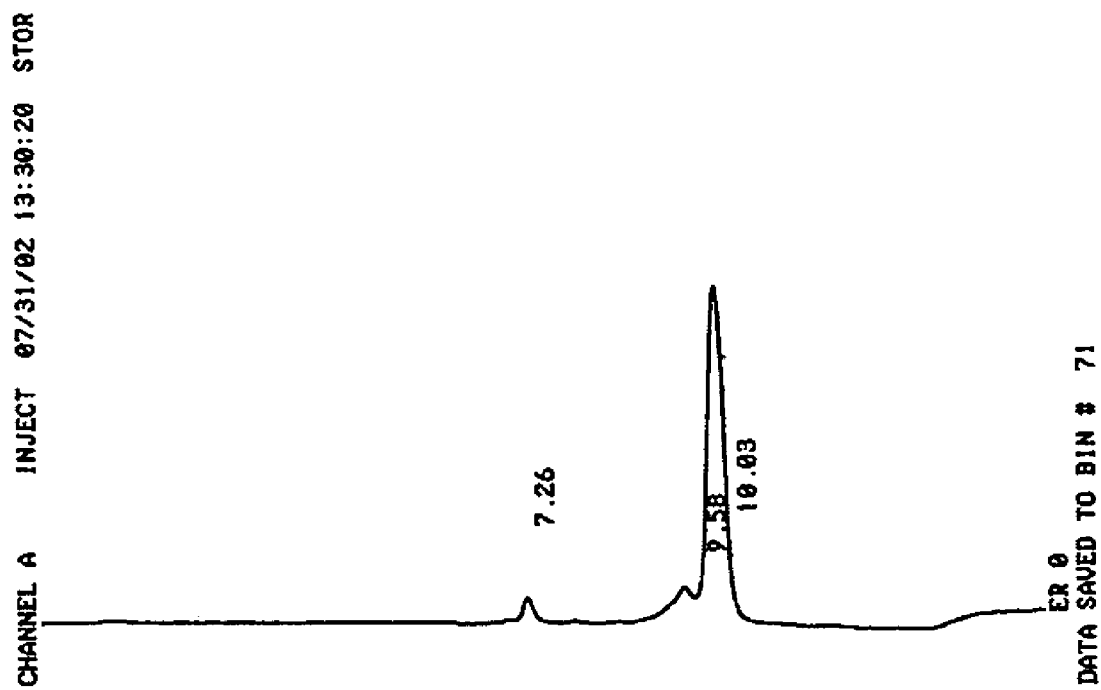
FIG. 2 is a graphic representation of an HPLC analysis of IMP 278 before being reacted with non-radioactive FDG (i.e., "cold" FDG).

Disclosed is a conjugate that includes a fluorinated carbohydrate molecule bound to a second molecule (e.g., a carrier, a targeting molecule, or an antibody molecule). Typically, the fluorinated carbohydrate molecule will include an isotope that may be useful in diagnostic or therapeutic methods, (e.g., F-18, F-19, F-17, F-20, and/or F-21).

The fluorinated carbohydrate molecule may include a variety of monosaccharides, their enantiomers, and/or derivatives including glucose, mannose, galactose, talose, gulose, idose, altrose, allose, ribose, arabinose, xylose, lyxose, erythrose, threose, and/or glyceraldehyde. The fluorinated carbohydrate molecule also may include ketose sugars (e.g., psicose, fructose, sorbose, and/or tagatose), disaccharides, (e.g., lactose, maltose, and/or sucrose), and/or polysaccharides. A particularly suitable fluorinated carbohydrate may be 2-Fluoro-2-Deoxy-D-Glucose. The fluorine atom may be F-18, although other isotopes may be used as well. Methods for synthesizing F-18 labeled carbohydrates have been described. See, e.g., Beuthien-Baumann et al., *Carbohydrate Res.* 2000, 327, 107-118; EP 0 167 103. The fluorinated carbohydrate molecule may be linked to a carrier by any suitable linkage, including a hydrazone linkage, a hydrazine linkage, an amino linkage, an amido linkage, an imino linkage, a sulfide linkage, an oxime linkage, a semicarbazone, a thiosemicarbazone linkage, a carbon—carbon linkage (e.g., formed by an ylide intermediate), or a boronic acid linkage.

In addition to fluorinated carbohydrate molecules such as FDG, precursors or derivatives of fluorinated carbohydrate molecules may be used to create the conjugate. For example, 1,3,4,6-tetra-O-Acetyl-2-O-trifluoromethanesulfonyl-β-D-mannopyranose or mannose triflate, may be linked to a second molecule by a hydrazone linkage, a hydrazine linkage, an amino linkage, an amido linkage, an imino linkage, a sulfide linkage, an oxime linkage, a semicarbazone, a thiosemicarbazone linkage, a carbon—carbon linkage (e.g., formed by an ylide intermediate), or a boronic acid linkage. The acetyl groups may be hydrolyzed prior to or after formation of the conjugate (e.g., by treating with sodium methoxide ($NaOCH_3$)).

In one claim, the fluorinated carbohydrate molecule is reacted directly with a second molecule such as a carrier. However, the fluorinated carbohydrate molecule also may be treated beforehand with additional reagents to facilitate conjugation. For example, it may be desirable to create aminated derivatives of the fluorinated carbohydrate. The aminated derivatives can then be reacted with a carrier, wherein a nucleophilic nitrogen atom attacks an electrophilic atom on the carrier, (e.g., a carbonyl carbon). Aminated derivatives may contain amino, amido, imino, aminooxy, and/or hydrazine groups, and the aminated derivative can form a nitrogen-containing linkage to the carrier.

The fluorinated carbohydrate molecule may be treated with halogenating agents to create a further substituted derivative of the fluorinated carbohydrate molecule. A precursor or derivative of FDG, such as 1,3,4,6,-tetra-O-Acetyl-2-O-trifluoromethanesulfonyl-β-D-mannopyranose or mannose triflate, may be treated with a chlorinating or brominating agent after the F-18 has been attached. These further fluorinated derivatives contain good leaving groups at the C1 position, and they can be used to link the fluorinated carbohydrate molecule to second molecules that may contain nucleophiles, such as the sulfur atom of a thiol group or the nitrogen atom of an amino group. The formation of adducts (i.e., conjugates) of FDG and 2-nitroimidazole has been described. See Patt et al., *Applied Radiat. and Isot* 2002, 57, 705-712. Another method for synthesizing the conjugate via thiol displacement includes (1) activating the acetal ester of a 1,3,4,6,-tetra-O-Acetyl-2-O-trifluoromethanesulfonyl-β-D-mannopyranose or mannose triflate molecule with $BF_3$ etherate; and (2) reacting the activated ester with the thiol group of a peptide or protein, (e.g., IMP 222), to create a sulfide linkage. The acetyl groups may be hydrolyzed to obtain the FDG-protein conjugate.

The second molecule may be any molecule that can be conjugated to the fluorinated carbohydrate molecule, and the second molecule may function as a carrier or a targeting molecule. In particular, peptide molecules may be suitable as carriers or targeting molecules. Suitable peptides may include by example (reading from amino to carboxy end): (1) $H_2N$—NH—$CH_2$—CO-Lys(X)-Tyr-Lys(X)—$NH_2$; (2) O=CH—CO-Lys(X)-Tyr-Lys(X)—$NH_2$; (3) $H_2N$—NH—$C_6H_4$—CO-Lys(X)-Tyr-Lys(X)—$NH_2$; (4) Ac-Cys-Lys(X)-Tyr-Lys(X)—$NH_2$ (SEQ ID NO: 1); (5) Gly-Lys(X)-Tyr-Lys(X)—$NH_2$ (SEQ ID NO: 2); (6) $H_2N$—NH—CS—NH—$C_6H_4$—CO-D-Lys (X)-D-Glu-D-Lys(X)—$NH_2$; (7) $H_2N$—NH—CS—NH—$C_6H_4$—CO-Lys(X)-Tyr-Lys(X)—$NH_2$; and/or (8) $H_2N$—O—$CH_2$—CO-Lys(X)-Tyr-Lys(X)—$NH_2$; wherein X is an antigenic molecule, a hapten, a hard acid chelator, and/or a soft acid chelator. A suitable peptide may also be described by the formula $H_2N$—NH—CS—NH—$C_6H_4$—CO-Aaa$_{(0-N)}$-Lys(X)-Aaa-Lys(X)—$NH_2$, wherein "Aaa" may be considered a "spacer amino acid," and "(0-N)" designates a number of amino acids from and including "0" up to and including "N." The peptide may be made from L amino acids D amino acids or a mixture of D and L amino acids. Haptens may include histamine-succinyl-glutamine ("HSG") and/or fluorescein isothiocyanate. Hard acid chelators may include DTPA, DOTA, NOTA (1,4,7-triaza-cyclononane-N,N',N''-triacetic acid), and TETA (p-bromoacetamido-benzyl-tetraethylaminetetraacetic acid). Where X is chosen to be DTPA, the preceding peptides (1)-(5) are designated IMP 209, IMP 213, IMP 221, IMP 222, and IMP 223, respectively. Where X is chosen to be HSG, peptide (6) is designated IMP 286. Soft acid chelators may include Tscg-Cys (thiosemicarbazonylglyoxylcysteine) and Tsca-Cys (thiosemicarbazinyl-acetylcysteine). The chelators may be complexed with metal ions, e.g., Indium-111. Where a carrier is a peptide, the carrier may be an antibody (e.g., a multispecific, multivalent, or bi-specific antibody). For peptides, the fluorinated carbohydrate may be linked to one or more amino acids present within the peptide. Other suitable peptides are described in U.S. patent application Ser. No. 10/150,654, incorporated herein by reference in its entirety.

The fluorinated carbohydrate molecule may be linked to a carrier or targeting molecule by a number of linkages. For example, the conjugate may comprise 2-Fluoro-2-Deoxy-D-Glucose linked to a carrier by a hydrazone/hydrazine linkage, an amino/imino linkage, an amido linkage, a sulfur-containing linkage (e.g., a sulfide linkage, a disulfide linkage), a semicarbazone linkage, a thiosemicarbazone, an oxime, a carbon—carbon linkage (e.g., formed by an ylide intermediate), or a boronic acid linkage.

For instance, one can react FDG with $NH_2$—O—$CH_2$—$CH_2$—NH-Boc or $NH_2$—NH—$CH_2$—$CH_2$—NH-Boc; reduce the oxime or the hydrazone; remove the Boc; and react the intermediate with an active ester to form an amide. In another example, one can react FDG with $NH_2$—O—$CH_2$—$CH_2$—S-Trt or $NH_2$—NH—$CH_2$—$CH_2$—S-Trt and then reduce the oxime or the hydrazone; remove the Trityl group; and react the intermediate with a thiol reactive group such as a maleimide or a chloro acetyl compound to link the sugar to a targeting molecule such as a peptide or a protein.

The fluorinated sugar molecule can also be functionalized to react with the second molecule. Methods for creating aminooxy-, hydrazide-, and thiosemicarbazide-functionalized saccharides have been described. See, e.g., Andreana, et al., *Organic Letts.* 2002, 4, 1863-1866; Liu et al., *J. Am Chem. Soc.* 2003, 125, 1702-1703; Rodriguez et al., *J. Org. Chem.* 1998, 63, 7134-7135. Functionalized saccharides, for example an aminooxy-, hydrazide-, and/or thiosemicarbazide-containing derivative of FDG, may be reacted with electrophilic groups on the second molecule (e.g., a carbonyl carbon within an aldehyde or keto group) to create an oxime, hydrazone, and/or thiosemicarbazone linkage. Where the second molecule is an amino acid or peptide, a carbonyl carbon of an aldehyde group or carboxyl group may be reacted with the functionalized carbohydrate to create a linkage. Alternatively, an α-ketocarbonyl amino acid or peptide may be created to provide a novel carbonyl carbon to link with the functionalized carbohydrate. The creation of α-ketocarbonyl peptides has been described. See, e.g., Papanikos et al., J. Am. Chem. Soc. 2001, 123, 2176-2181; Wang et al., Proc. Natl. Acad. Sci. 2003, 1, 56-61.

Figure 9:
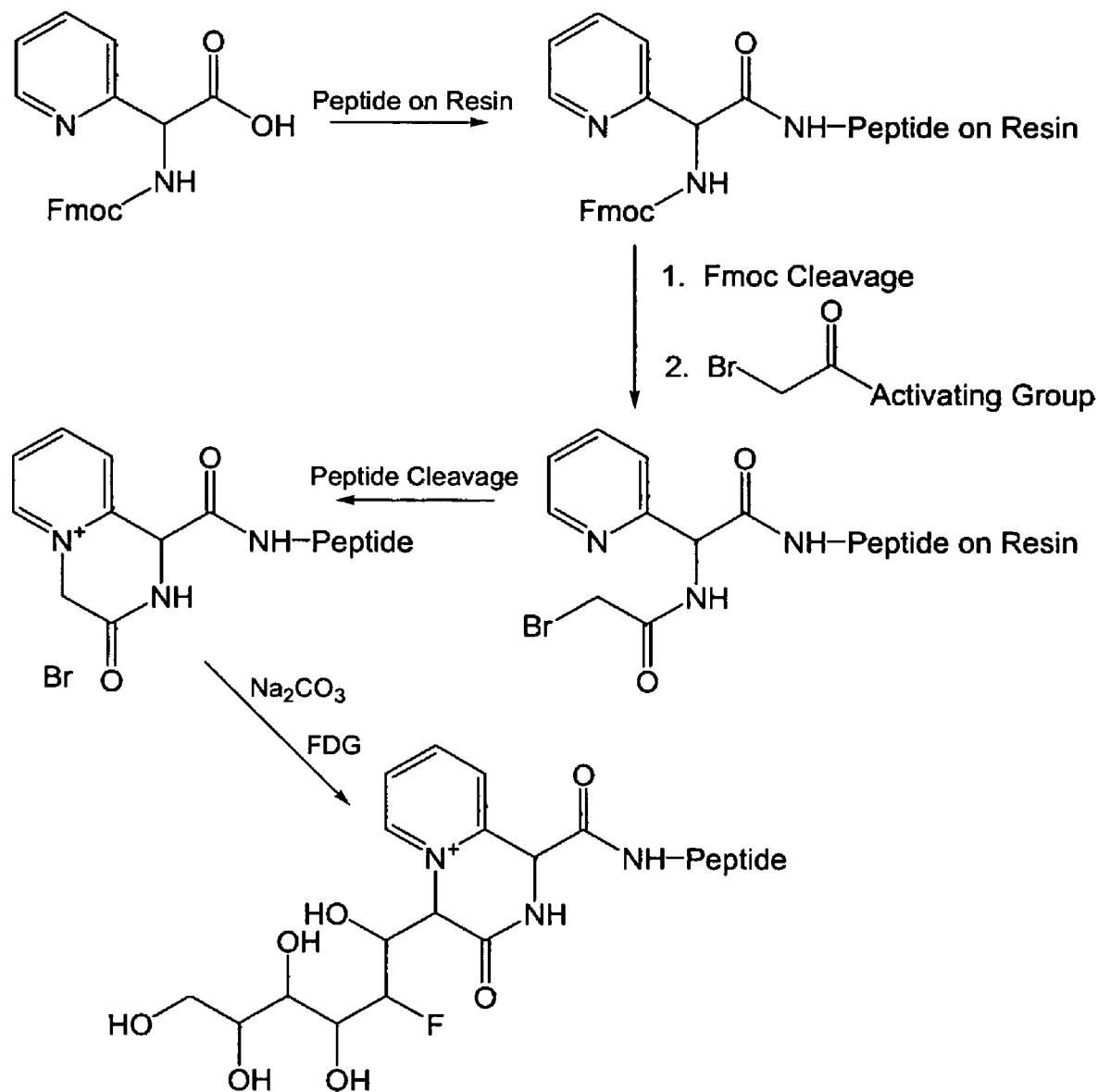
FIG. 9 is a schematic representation of the creation of an FDG-peptide conjugate by a nitrogen-ylide intermediate.

In another claim, the conjugate is formed by a water active ylide reaction. Ylide reactions have been described. See, e.g., Kostik et al., J. Org. Chem. 2001, 66, 2618-2623. An example condensation is shown in FIG. 9. In the example, a nitrogen-ylide is activated with carbonate and condensed with FDG to create a carbon—carbon bond between the FDG and a peptide.

Use of the Conjugate in Pretargeting Methods

The disclosed conjugates may be useful in pretargeting methodologies. Pretargeting methodologies have received considerable attention for cancer imaging and therapy. Unlike direct targeting systems where an effector molecule (e.g., a radionuclide or a drug linked to a small carrier) is directly linked to the targeting agent, in pretargeting systems, the effector molecule is given some time after the targeting agent. This allows time for the targeting agent to localize in tumor lesions and, more importantly, clear from the body. Since most targeting agents have been antibody proteins, they tend to clear much more slowly from the body (usually days) than the smaller effector molecules (usually in minutes). In direct targeting systems involving therapeutic radionuclides, the body, and in particular the highly vulnerable red marrow, is exposed to the radiation all the while the targeting agent is slowly reaching its peak levels in the tumor and clearing from the body. In a pretargeting system, the radionuclide is usually bound to a small "effector" molecule, such as a chelate or peptide, which clears very quickly from the body, and thus exposure of normal tissues is minimized. Maximum tumor uptake of the radionuclide is also very rapid because the small molecule efficiently transverses the tumor vasculature and binds to the primary targeting agent. Its small size may also encourage a more uniform distribution in the tumor.

Desirably, the targetable construct includes a peptide having at least 2 units of a recognizable hapten. Examples of recognizable haptens include, but are not limited to, histamine succinyl glycine (HSG) or DTPA (e.g., chelating $^{111}$In). The targetable construct may be conjugated to a variety of agents useful for treating or identifying diseased tissue, (e.g., F-18). Examples of conjugated agents include, but are not limited to, chelators, metal chelate complexes, hormones, cytokines and other immunomodulators, drugs (e.g., camptothecins, anthroacyclines, etc.), toxins (e.g., ricin, abrin, ribonuclease (e.g., RNase), DNase I, Staphylococcal enterotoxin-A, pokeweed antiviral protein, gelonin, diphtherin toxin, Pseudomonas exotoxin, Pseudomonas endotoxin, aplidin) and other effector molecules. Additionally, enzymes useful for activating a prodrug or increasing the target-specific toxicity of a drug can be conjugated to the targetable construct. Thus, the use of bsAb which are reactive to a targetable construct allows a variety of therapeutic and diagnostic applications to be performed without raising new bsAb for each application.

Bi-specific antibody (bsAb) pretargeting, using the disclosed conjugate as a targeting construct, represents a potentially non-immunogenic, highly selective alternative for diagnostic and therapeutic applications. The bsAb pretargeting system described herein represents an additional significant advantage over other pretargeting systems in that it potentially can be developed for use with a variety of different imaging or therapeutic agents. The flexibility of this system is based on use of an antibody directed against histamine-succinyl-glycl (HSG) and the development of peptides containing the HSG residue. HSG-containing peptides were synthesized with either DOTA for the chelation of $^{111}$In, $^{90}$Y, or $^{177}$Lu or a technetium/rhenium chelate. Alternatively, an antibody directed against In-DTPA can be used with In-DTPA and/or peptides developed that contain In-DTPA. For pretargeting, these peptides were used in combination with bi-specific antibodies using the anti-HSG Fab' chemically stabilized with the Fab' of either an anti-carcinoembryonic antigen (CEA) or an anti-colon-specific antigen-p (CSAp) antibody to provide tumor targeting capability for tumors expressing these antigens. However, other antigen targets may include diverse tumor-associated antigens known in the art, such as against CD4, CD5, CD8, CD14, CD15, CD19, CD20, CD21, CD22, CD23, CD25, CD30, CD33, CD37, CD38, CD40, CD40L, CD45, CD46, CD52, CD54, CD74, CD80, CD126, HLA-DR, Ia, Ii, B7, HM1.24, MUC 1, MUC 2, MUC 3, MUC 4, NCA, EGFR, HER 2/neu, PAM-4, BrE3, TAG-72 (B72.3, CC49), EGP-1 (e.g., RS7), EGP-2 (e.g., 17-1A and other Ep-CAM targets), Le(y) (e.g., B3), A3, KS-1, S100, IL-2, IL-6, T101, insulin-like growth factor-1 ("ILGF-1"), necrosis antigens, folate receptors, angiogenesis markers (e.g., VEGF, placenta growth factor ("PlGF"), etc.), tenascin, fibronectin, PSMA, PSA, tumor-associated cytokines, MAGE and/or fragments thereof. Tissue-specific antibodies (e.g., against bone marrow cells, such as CD34, CD74, etc., parathyroglobulin antibodies, etc.) as well as antibodies against non-malignant diseased tissues, such as fibrin of clots, macrophage antigens of atherosclerotic plaques (e.g., CD74 antibodies), antibodies against ischemic foci (e.g., anti-granulocyte antibodies, such as MN-3 or other NCA-cross reactive antibodies, such as anti-NCA-95 antibodies (i.e., anti-CEACAM8)), antibodies against neurological lesions, such as the amyloid deposits accumulating in the brain of Alzheimer patients, and also specific pathogen antibodies (e.g., against bacteria, viruses, and parasites) are well known in the art. As such, the diagnostic method may also be useful for diagnosing a cardiovascular disease, an infectious disease, an inflammatory disease, an autoimmune disease, and/or a neurological disease. Antigens that are characteristic for the various diseases may be chosen as a target by the bi-specific antibody.

Many antibodies and antibody fragments which bind markers produced by or associated with tumors or infectious lesions, including viral, bacterial, fungal and parasitic infections and/or diseases, and antigens and products associated with such microorganisms have been disclosed, inter alia, in Hansen et al., U.S. Pat. No. 3,927,193 and Goldenberg U.S. Pat. Nos. 4,331,647, 4348,376, 4,361,544, 4,468,457, 4,444, 744, 4,460,459 and 4,466,561, 4,624,846, and in related applications U.S. Ser. Nos. 60/609,607 and 60/633,999, the disclosures of all of which are incorporated in their entireties herein by reference.

Infectious diseases include those caused by invading microbes or parasites. As used herein, "microbe" denotes virus, bacteria, rickettsia, mycoplasma, protozoa, fungi and like microorganisms, "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like, including helminths, while "infectious agent" or "pathogen" denotes both microbes and parasites.

The compositions of the present invention can be used to treat immune dysregulation disease and related autoimmune diseases. Autoimmune diseases are a class of diseases associated with a B-cell disorder. Examples include myasthenia gravis, lupus nephritis, lupus erythematosus, and rheumatoid arthritis, Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

The compositions of the present invention may be particularly useful in the method of treating autoimmune disorders, disclosed in pending U.S. Ser. No. 09/590,284 filed on Jun. 9, 2000 entitled "Immunotherapy of Autoimmune Disorders using Antibodies that Target B-Cells," which is incorporated in its entirety by reference.

The compositions of the present invention may also be used to diagnose or treat malignant diseases. Antigens present on the targeted tissue may include carcinoembryonic antigen, tenascin, fibronectin, epidermal growth factor receptor, platelet derived growth factor receptor, fibroblast growth factor receptors, vascular endothelial growth factor receptors, gangliosides, insuline-like growth factors, and HER2/neu receptors.

A particular useful bi-specific antibody may comprise the Fv of an antibody that is reactive with CSAp, such as MAb Mu-9, and the Fv of MAb 679 (anti-HSG). Mu-9 and/or 679 may be murine, human, chimerized, or humanized. The bi-specific antibody may comprise one or more of the CDRs of Mu-9 or one or more of the CDRs of 679. Further, the bi-specific antibody may comprise a fusion protein.

Another particularly useful bi-specific antibody may comprise the Fv of a Class III anti-CEA antibody, such as MAb MN-14 (anti-CEA), and the Fv of MAb 679. MN-14 and/or 679 may be murine, human, chimerized, or humanized. The bi-specific antibody may comprise one or more of the CDRs of MN-14 or one or more of the CDRs of 679. Further, the bi-specific antibody may comprise a fusion protein.

Use of the Conjugate in Diagnostic and Therapeutic Methods

Additionally encompassed is a method for detecting and/or treating target cells, tissues or pathogens in a mammal, comprising administering to a subject a conjugate that includes an effective amount of an antibody or antibody fragment comprising at least one arm that binds a targeted tissue. The antibody or antibody fragment may include at least one other arm that binds a targetable construct, which may also be administered to the subject. The targetable construct and/or antibody or antibody fragment may be labeled by using the disclosed method. For example, the disclosed conjugate may comprise the targetable construct or the antibody or antibody fragment. The methods may be used to diagnose and treat a variety of diseases, including but not limited to, a malignant disease, an infectious disease, an inflammatory disease, an autoimmune disease, a cardiovascular disease, and/or a neurological disease. The aforementioned disease may be diagnosed and/or treated particularly by targeting tissue that includes antigens as disclosed herein, or antigens that are recognized as being associated with the aforementioned diseases. Targeting and/or pretargeting methods are described in 60/342,104, filed Dec. 26, 2001, and incorporated herein by reference in its entirety.

The diagnostic/therapeutic method can be used to detect and treat cells that have been exposed to a pathogen. As used herein, the term "pathogen" includes, but is not limited to fungi (e.g., *Microsporum, Trichophyton, Epidermophyton, Sporothrix schenckii, Cryptococcus neoformans, Coccidioides immitis, Histoplasma Capsulatum, Blastomyces dermatitidis, Candida albicans*), viruses (e.g., human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus), parasites, bacteria (e.g., Anthrax *bacillus, Streptococcus agalactiae, Legionella pneumophilia, Streptococcus pyogenes, Escherichia coli, Neisseria gonorrhoeae, Neisseria meningitidis, Pneumococcus, Hemophilis influenzae B, Treponema pallidum*, Lyme disease spirochetes, *Pseudomonas aeruginosa, Mycobacterium leprae, Brucella abortus, Mycobacterium tuberculosis* and Tetanus toxin); mycoplasma (e.g., *Mycoplasma arthritidis, M. hyorhinis, M. orale, M. arginini, Acholeplasma laidlawii, M. salivarum*, and *M. pneumoniae*) and protozoans (e.g., *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides corti*). See U.S. Pat. No. 5,332,567, incorporated herein by reference in its entirety. Additional listings of representative disease-causing infectious organisms to which antibodies can be developed for use in this invention are contained in the second and subsequent editions of Davis et al., "Microbiology" (Harper & Row, New York, 1973 and later), and are well known to one of ordinary skill in the art.

Examples of autoimmune diseases that could be treated by the methods of the invention include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis,thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, and fibrosing alveolitis.

The methods of the invention, including methods for treating autoimmune disorders and neoplastic disorders may be used to treat disorders such as cardiovascular diseases and inflammation. These disorders include myocardial infarction, ischemic heart disease, clots, emboli, and atherosclerotic plaques. For example, the detection may be used to detect damaged heart and vascular tissue. The cell ablation methods may be used for targeting diseased heart tissue. Inflammation can be detected or treated with anti-granulocyte (e.g., anti-CD66, anti-CD33, anti-CD45), anti-lymphocyte (anti-B- or anti-T-cell antibodies), and/or anti-monocyte antibodies (e.g., anti-Ia or anti-CD74 antibody).

Without limitation the present compositions and methods can be used for therapy and/or diagnosis or imaging for cardiovascular lesions (infarcts, clots, emboli, atherosclerotic plaques), other pathological lesions (e.g., amyloid in amyloidosis and in Alzheimer's disease), cancers (e.g., leukemias, lymphomas, sarcomas, melanomas, carcinomas, gliomas, skin cancers), infectious diseases (e.g., bacterial, rickettsial, fungal, parasitical, and viral pathogens), inflammation (e.g., autoimmune diseases, such as rheumatoid arthritis, systemic erythematosis, multiple sclerosis), displaced or ectopic normal tissues and cells (e.g., endometrium, thymus, spleen, parathyroid), normal tissue ablation (e.g., endometriosis, bone marrow, spleen).

Neurological disease, (e.g., brain tumors), may be diagnosed or treated by using the disclosed conjugates. In particular, antibodies or antibody fragments that recognize antigens such as tenascin, fibronectin, epidermal growth factor receptor, platelet derived growth factor receptor, fibroblast growth factor receptors, vascular endothelial growth factor receptors, gangliosides, and HER2/neu receptors, may be used to diagnose or treat a neurological malignancy.

Chemotherapeutic agents, for the purpose of this disclosure, include all known chemotherapeutic agents. Known chemotherapeutic agents include, at least, the taxanes, nitrogen mustards, ethylenimine derivatives, alkyl sulfonates, nitrosoureas, triazenes; folic acid analogs, pyrimidine analogs, purine analogs, vinca alkaloids, antibiotics, enzymes, platinum coordination complexes, substituted urea, methyl hydrazine derivatives, adrenocortical suppressants, or antagonists. More specifically, the chemotherapeutic agents may be steroids, progestins, estrogens, antiestrogens, or androgens. Even more specifically, the chemotherapy agents may be aplidin, azaribine, anastrozole, azacytidine, bleomycin, bryostatin-1, busulfan, camptothecin, 10-hydroxycamptothecin, carmustine, chlorambucil, cisplatin, irinotecan (CPT-11), SN-38, carboplatin, celebrex and other COX-2 inhibitors, cladribine, cyclophosphamide, cytarabine, dacarbazine, docetaxel, dactinomycin, daunorubicin, dexamethasone, diethylstilbestrol, doxorubicin, ethinyl estradiol, estramustine, etoposide, floxuridine, fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, methotrexate, mitoxantrone, mithramycin, mitomycin, mitotane, phenyl butyrate, prednisone, procarbazine, paclitaxel, pentostatin, semustine streptozocin, tamoxifen, taxanes, taxol, testosterone propionate, thalidomide, thioguanine, thiotepa, teniposide, topotecan, uracil mustard, velcade, vinblastine, vinorelbine or vincristine.

Antibodies and Antibody Fragments

Also provided herein are antibodies and antibody fragments which may be labeled by the disclosed method and/or used in conjugation with a targeting construct in diagnostic/therapeutic methods. The labeling method described herein may be used to create labeled antibodies or fragments that comprise a fluorinated carbohydrate conjugate. The antibody fragments are antigen binding portions of an antibody, such as F(ab')$_2$, F(ab)$_2$, Fab', Fab, and the like. The antibody fragments bind to the same antigen that is recognized by the intact antibody. For example, an anti-CD22 monoclonal antibody fragment binds to an epitope of CD22.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the "hypervariable region." Three of these so-called "hypervariable" regions or "complementarity-determining regions" (CDR) are found in each variable region of the light or heavy chain. Each CDR is flanked by relatively conserved framework regions (FR). The FR are thought to maintain the structural integrity of the variable region. The CDRs of a light chain and the CDRs of a corresponding heavy chain form the antigen-binding site. The "hypervariability" of the CDRs accounts for the diversity of specificity of antibodies.

Targetable Constructs

The targetable construct can be of diverse structure, but is selected not only to diminish the elicitation of immune responses, but also for rapid in vivo clearance when used within the bsAb targeting method. Hydrophobic agents are best at eliciting strong immune responses, whereas hydrophilic agents are preferred for rapid in vivo clearance, thus, a balance between hydrophobic and hydrophilic needs to be established. This is accomplished, in part, by relying on the use of hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may be used. The labeling method described herein may be used to create labeled targeting molecules that comprise a fluorinated carbohydrate conjugate.

The targetable construct may include a peptide backbone. having as few as two amino-acid residues, with preferably two to ten amino acid residues, and may be coupled to other moieties such as chelating agents. The targetable construct should be a low molecular weight construct, preferably having a molecular weight of less than 50,000 daltons, and advantageously less than about 20,000 daltons, 10,000 daltons or 5,000 daltons, including any metal ions that may be bound to the chelating agents. More usually, the antigenic peptide of the targetable construct will have four or more residues.

The haptens of the targetable construct also provide an immunogenic recognition moiety, for example, a chemical hapten. Using a chemical hapten, preferably the HSG hapten, high specificity of the construct for the antibody is exhibited. This occurs because antibodies raised to the HSG hapten are known and can be easily incorporated into the appropriate bsAb. Thus, binding of the haptens to the peptide backbone would result in a targetable construct that is specific for the bsAb or bsFab.

The targetable construct also may include unnatural amino acids, e.g., D-amino acids, into the peptide backbone structure to ensure that, when used with the final bsAb/construct system, the arm of the bsAb which recognizes the targetable construct is completely specific. The conjugate also may include other backbone structures such as those constructed from non-natural amino acids and peptoids.

The peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts *Protective Groups in Organic Synthesis*, 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity.

Chelates on the Targetable Construct

The presence of hydrophilic chelate moieties on the targetable construct helps to ensure rapid in vivo clearance. In addition to hydrophilicity, chelators are chosen for their metal-binding properties, and may be changed at will since, at least for those targetable constructs whose bsAb epitope is part of the peptide or is a non-chelate chemical hapten, recognition of the metal-chelate complex is no longer an issue. The metal chelator may be used to label the targetable constructs with nuclides in addition to the nuclide that may be present on FDG, (e.g., F-18), where the targetable construct comprises a fluorinated carbohydrate conjugate.

Particularly useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$Bi, and $^{225}$AC for radio-imaging and RAIT. The same chelators, when complexed with non-radioactive metals such as Mn, Fe and Gd for use with MRI, when used along with the disclosed bsAbs. Macrocyclic chelators such as NOTA (1,4,7-triaza-cyclononane-N,N',N''-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelators may be used with numerous radiometals, and are also useful as certain cold metal complexes for bsAb-directed immuno-phototherapy. Also, more than one type of chelator may be conjugated to the targetable construct to bind multiple metal ions, e.g., cold ions, diagnostic radionuclides and/or therapeutic radionuclides.

Particularly useful therapeutic radionuclides that can be bound to the chelating agents of the targetable construct include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and/or $^{211}$Pb. The therapeutic radionuclide preferably has a decay energy in the range of 25 to 10,000 keV. Decay energies of useful beta-particle-emitting nuclides are preferably 25-5,000 keV, more preferably 100-4,000 keV, and most preferably 500-2, 500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-9,000 keV, more preferably 3,000-8,000 keV, and most preferably 4,000-7,000 keV.

Chelators such as those disclosed in U.S. Pat. No. 5,753, 206, (incorporated herein by reference), especially thiosemicarbazonylglyoxylcysteine(Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a hard acid chelator like DTPA for In(III) cations, and a soft acid chelator (e.g, thiol-containing chelator such as Tscg-Cys) for Tc cations. Because antibodies to a di-DTPA hapten are known (Barbet '395, supra) and are readily coupled to a targeting antibody to form a bsAb, it is possible to use a peptide hapten with cold di-DTPA chelator and another chelator for binding a radioisotope, in a pretargeting protocol, for targeting the radioisotope. One example of such a peptide is Ac-Lys(DTPA)-Tyr-Lys (DTPA)-Lys (Tscg-Cys)-NH$_2$ (SEQ ID NO:3) (IMP 192). This peptide can be preloaded with In(III) and then labeled with 99-m-Tc cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the targeting construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker or targeting construct for eventual capture by a pretargeted bsAb. Chelators are coupled to the peptides of the targetable construct using standard chemistries.

Labeled Antibodies and/or Targetable Constructs for Diagnostic/Therapeutic Methods The labeling method may be used to create antibodies (e.g., multispecific antibodies, bi-specific antibodies, multivalent antibodies) or fragments of antibodies that are useful for diagnostic or therapeutic methods, (e.g., antibodies or fragments that are conjugated to F-18, 2-Fluoro-2-Deoxy-D-Glucose). Alternatively, the labeling method may be used to create a targetable construct (e.g., labeled with F-18, FDG), and the targetable construct may be used together with an antibody or an antibody fragment in a diagnostic or therapeutic method. The antibody and/or targeting construct may include one or more of the same or different diagnostic and/or therapeutic nuclides.

It should be noted that much of the discussion presented hereinbelow focuses on the use of the conjugate as a targetable construct together with bi-specific antibodies in the context of diagnosing and/or treating diseased tissue. The conjugate may be useful together with bi-specific antibodies and in treating and/or imaging normal tissue and organs using the methods described in U.S. Pat. Nos. 6,126,916; 6,077, 499; 6,010,680; 5,776,095; 5,776,094; 5,776,093; 5,772,981; 5,753,206; 5,746,996; 5,697,902; 5,328,679; 5,128,119; 5,101,827; and 4,735,210, which are incorporated herein by reference. As used herein, the term "tissue" refers to tissues, including but not limited to, tissues from the ovary, thymus, parathyroid, bone marrow or spleen. An important use when targeting normal tissues is to identify and treat them when they are ectopic (i.e., displaced from their normal location), such as in endometriosis.

The conjugate may be used as a targetable construct in methods of diagnosis that include: (A) administering to the subject an antibody or antibody fragment having at least one arm that binds a targeted tissue and at least one other arm that binds the conjugate as a targetable construct; (B) optionally, administering to the subject a clearing composition, and allowing the composition to clear non-localized antibodies or antibody fragments from circulation; and (C) administering to the subject the conjugate as a targetable which includes at least one diagnostic agent. The antibody or antibody fragment may be multispecific, bi-specific, and/or multivalent. The diagnostic agent may be a radionuclide such as F-18. In particular, the method may be used to perform positron-emission tomography (PET).

At the time of administration, the targeting construct preferably has a specific activity of $10mCi/6.0\times10^{-5}$ mmol or ~167 Ci/mmol. A desirable dose may be 60 mg/$6.0\times10^{-4}$ mmol, and the amount of FDG used per patient is approximately 10 mCi. Typically, the amount of targeting construct administered is one tenth the molar amount of antibody administered.

The administration of a bsAb and the targetable construct discussed above may be conducted by administering the bsAb at some time prior to administration of the therapeutic agent which is associated with the linker moiety. The doses and timing of the reagents can be readily devised by a skilled artisan, and are dependent on the specific nature of the reagents employed. If a bsAb-F(ab')$_2$ derivative is given first, then a waiting time of 1-6 days before administration of the targetable construct may be appropriate. If an IgG-Fab' bsAb conjugate is the primary targeting vector, then a longer waiting period before administration of the linker moiety may be indicated, in the range of 3-15 days. Alternatively, the bsAb and the targetable construct may be administered substantially at the same time in either a cocktail form or by administering one after the other.

Additional Diagnostic and Therapeutic Reagents

In addition to isotopes incorporated by the disclosed method, a wide variety of additional diagnostic and therapeutic reagents may be present on the targetable construct and/or antibody. Generally, diagnostic and therapeutic agents can include isotopes, drugs, toxins, cytokines, conjugates with cytokines, hormones, growth factors, conjugates, radionuclides, contrast agents, metals, cytotoxic drugs, and immune modulators. For example, gadolinium metal is used for magnetic resonance imaging and fluorochromes can be conjugated for photodynamic therapy. Moreover, contrast agents can be MRI contrast agents, such as gadolinium ions, lanthanum ions, manganese ions, iron, chromium, copper, cobalt, nickel, dysprosium, rhenium, europium, terbium, holmium, neodymium or other comparable label, CT contrast agents, and ultrasound contrast agents. Additional diagnostic agents can include fluorescent labeling compounds such as fluorescein isothiocyanate, rhodamine, phycoerytherin, phycocyanin, allophycocyanin, o-phthaldehyde and fluorescamine, chemiluminescent compounds including luminol, isoluminol, an aromatic acridinium ester, an imidazole, an acridinium salt and an oxalate ester, and bioluminescent compounds including luciferin, luciferase and aequorin. Radionuclides can also be used as diagnostic and/or therapeutic agents, including for example, $^{90}$Y, $^{111}$In, 124I, $^{131}$I, $^{99m}$Tc, $^{186}$Re, $^{188}$Re, $^{177}$Lu, $^{67}$CU, $^{212}$Bi, $^{213}$Bi, $^{211}$At, and/or $^{18}$F.

Therapeutic agents also include, for example, chemotherapeutic drugs or prodrugs such as vinca alkaloids, anthracyclines, epidophyllotoxins, taxanes, antimetabolites, alkylating agents, antibiotics, Cox-2 inhibitors, antimitotics, antiangiogenic and apoptotic agents, particularly doxorubicin, methotrexate, taxol, CPT-11, SN-38, camptothecins, aplidin, and others from these and other classes of anticancer agents. Other useful therapeutic agents for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable therapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable therapeutic agents, such as experimental drugs, are known to those of skill in the art. Therapeutic agents may also include, without limitation, others drugs, prodrugs and/or toxins. The terms "drug," "prodrug," and "toxin" are defined throughout the specification. The terms "diagnostic agent" or "diagnosis" include, but are not limited to, detection agent, detection, or localization.

When the targetable construct includes a diagnostic agent, the bsAb is preferably administered prior to administration of the targetable construct with the diagnostic agent. After sufficient time has passed for the bsAb to target to the diseased tissue, the diagnostic agent is administered, by means of the targetable construct, so that imaging can be performed. Tumors can be detected in body cavities by means of directly or indirectly viewing various structures to which light of the appropriate wavelength is delivered and then collected, or even by special detectors, such as radiation probes or fluorescent detectors, and the like. Lesions at any body site can be viewed so long as nonionizing radiation can be delivered and recaptured from these structures. For example, PET which is a high resolution, non-invasive, imaging technique can be used with the inventive antibodies and targetable constructs for the visualization of human disease. In PET, 511 keV gamma photons produced during positron annihilation decay are detected. X-ray, computed tomography (CT), MRI and gamma imaging (e.g., Single Photon Emission Computed Tomography (SPECT)) may also be utilized through use of a diagnostic agent that functions with these modalities.

As discussed earlier, the targetable construct may include radioactive diagnostic agents that emit 25-10,000 keV gamma-, beta-, alpha- and auger-particles and/or positrons. Examples of such agents include, but are not limited to $^{18}$F, $^{45}$Ti, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

The antibody or bi-specific antibody also can be conjugated with other diagnostic agents such as photoactive agents or dyes to form an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), *Photodynamic Therapy of Tumors and Other Diseases* (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288: 471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present diagnostic/therapeutic methods may include the therapeutic use of immunoconjugates comprising photoactive agents or dyes. Endoscopic methods of detection and therapy are described in U.S. Pat. Nos. 4,932, 412; 5,525,338; 5,716,595; 5,736,119; 5,922,302; 6,096,289; and 6,387,350, which are incorporated herein by reference in their entirety.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. Ultrasound contrast material may also by used including dextran and liposomes, particularly gas-filled liposomes.

In one claim, an immunomodulator, such as a cytokine, may be conjugated to the targetable construct, antibody, or antibody fragment by a linker or through other methods known by those skilled in the art. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, interferon-γ, TNF-α, and the like.

The targetable construct or antibody may also be conjugated to an enzyme capable of activating a drug/prodrug at the target site or improving the efficacy of a normal therapeutic by controlling the body's detoxification pathways. For example, following administration of the bsAb, an enzyme conjugated to the targetable construct having a low MW hapten may be administered. After the enzyme is pretargeted to the target site by bsAb:targetable construct binding, a cytotoxic drug is injected that is known to act at the target site. The drug may be one which is detoxified by the mammal's ordinary detoxification processes to form an intermediate of lower toxicity. For example, the drug may be converted into the potentially less toxic glucuronide in the liver. The detoxified intermediate can then be reconverted to its more toxic form by the pretargeted enzyme at the target site, and this enhances cytotoxicity at the target site.

Alternatively, an administered prodrug can be converted to an active drug by the pretargeted enzyme. The pretargeted enzyme improves the efficacy of the treatment by recycling the detoxified drug. This approach can be adopted for use with any enzyme-drug pair. Alternatively, the targetable construct with enzyme can be mixed with the targeting bsAb prior to administration to the patient. After a sufficient time has passed for the bsAb:targetable construct- conjugate to localize to the target site and for unbound targetable construct to clear from circulation, a prodrug is administered. As discussed above, the prodrug is then converted to the drug in situ by the pre-targeted enzyme.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in U.S. Pat. No. 5,851,527, to Hansen.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase See, e.g., *Arcamone Cancer Res.* 45:5995 (1985). Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the disclosed diagnostic/therapeutic methods.

The prodrug CPT-11 (irinotecan) is converted in vivo by carboxylesterase to the active metabolite SN-38. One application of the disclosed diagnostic/therapeutic method, therefore, is to use a bsAb targeted against a tumor and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the disclosed diagnostic/therapeutic methods. See, e.g., Potter et al., *Cancer Res.* 58:2646-2651 (1998) and Potter et al., *Cancer Res.* 58:3627-3632 (1998).

Etoposide is a widely used cancer drug that is detoxified to a major extent by formation of its glucuronide and is within the scope of the disclosed diagnostic/therapeutic methods. See, e.g., Hande et al. *Cancer Res.* 48:1829-1834 (1988). Glucuronide conjugates can be prepared from cytotoxic drugs and can be injected as therapeutics for tumors pretargeted with mAb-glucuronidase conjugates. See, e.g., Wang et al. *Cancer Res.* 52:4484-4491 (1992). Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al. *J. Med Chem.* 40:4013-4018 (1997). Other examples of prodrug/enzyme pairs that can be used within the present diagnostic/therapeutic methods, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

The enzyme capable of activating a prodrug at the target site or improving the efficacy of a normal therapeutic by controlling the body's detoxification pathways may alternatively be conjugated to the hapten. The enzyme-hapten conjugate is administered to the subject following administration of the pre-targeting bsAb and is directed to the target site. After the enzyme is localized at the target site, a cytotoxic drug is injected, which is known to act at the target site, or a prodrug form thereof which is converted to the drug in situ by the pretargeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processes. The pretargeted enzyme improves the efficacy of the treatment by recycling the detoxified drug. This approach can be adopted for use with any enzyme-drug pair.

In an alternative claim of the diagnostic/therapeutic method, the enzyme-hapten conjugate can be mixed with the targeting bsAb prior to administration to the patient. After a sufficient time has passed for the enzyme-hapten-bsAb conjugate to localize to the target site and for unbound conjugate to clear from circulation, a prodrug is administered. As discussed above, the prodrug is then converted to the drug in situ by the pre-targeted enzyme.

In another claim of the diagnostic/therapeutic method, the peptide backbone of the targetable construct is conjugated to a prodrug. The pre-targeting bsAb is administered to the patient and allowed to localize to the target and substantially clear circulation. At an appropriate later time, a targetable construct comprising a prodrug, for example poly-glutamic acid (SN-38-ester)$_{10}$, is given, thereby localizing the prodrug specifically at the tumor target. It is known that tumors have increased amounts of enzymes released from intracellular sources due to the high rate of lysis of cells within and around tumors. A practitioner can capitalize on this fact by appropriately selecting prodrugs capable of being activated by these enzymes. For example, carboxylesterase activates the prodrug poly-glutamic acid (SN-38-ester)$_{10}$ by cleaving the ester bond of the poly-glutamic acid (SN-38-ester)$_{10}$ releasing large concentrations of free SN-38 at the tumor. Alternatively, the appropriate enzyme also can be targeted to the tumor site.

After cleavage from the targetable construct, the drug is internalized by the tumor cells. Alternatively, the drug can be internalized as part of an intact complex by virtue of cross-linking at the target. The targetable construct can induce internalization of tumor-bound bsAb and thereby improve the efficacy of the treatment by causing higher levels of the drug to be internalized.

A variety of prodrugs can be conjugated to the targetable construct. The above exemplifications of polymer use are concerned with SN-38, the active metabolite of the prodrug CPT-11 (irinotecan). SN-38 has an aromatic hydroxyl group that was used in the above descriptions to produce aryl esters susceptible to esterase-type enzymes. Similarly the camptothecin analog topotecan, widely used in chemotherapy, has an available aromatic hydroxyl residue that can be used in a similar manner as described for SN-38, producing esterase-susceptible polymer-prodrugs.

Doxorubicin also contains aromatic hydroxyl groups that can be coupled to carboxylate-containing polymeric carriers using acid-catalyzed reactions similar to those described for the camptothecin family. Similarly, doxorubicin analogs like daunomycin, epirubicin and idarubicin can be coupled in the same manner. Doxorubicin and other drugs with amino 'chemical handles' active enough for chemical coupling to polymeric carriers can be effectively coupled to carrier molecules via these free amino groups in a number of ways. Polymers bearing free carboxylate groups can be activated in situ (EDC) and the activated polymers mixed with doxorubicin to directly attach the drug to the side-chains of the polymer via amide bonds. Amino-containing drugs can also be coupled to amino-pendant polymers by mixing commercially available and cleavable cross-linking agents, such as ethylene glycobis(succinimidylsuccinate) (EGS, Pierce Chemical Co., Rockford, Ill.) or bis-[2-(succinimido-oxycarbonyloxy) ethyl]sulfone (BSOCOES, Molecular Biosciences, Huntsville, Ala.), to cross-link the two amines as two amides after reaction with the bis(succinimidyl) ester groups. This is advantageous as these groups remain susceptible to enzymatic cleavage. For example, (doxorubicin-EGS)$_n$-poly-lysine remains susceptible to enzymatic cleavage of the diester groups in the EGS linking chain by enzymes such as esterases. Doxorubicin also can be conjugated to a variety of peptides, for example, HyBnK(DTPA)YK(DTPA)-NH$_2$, using established procedures (HyBn=p-H$_2$NNHC$_6$H$_4$CO$_2$H). See Kaneko et al., *J. Bioconjugate Chem.*, 2:133-141, 1991.

In still other claims, the bi-specific antibody-directed delivery of therapeutics or prodrug polymers to in vivo targets can be combined with bi-specific antibody delivery of radionuclides, such that combination chemotherapy and radioimmunotherapy is achieved. Each diagnostic/therapeutic agent can be conjugated to a targetable construct and administered simultaneously, or the nuclide can be given as part of a first targetable construct and the drug given in a later step as part of a second targetable construct. In one simple claim, a peptide containing a single prodrug and a single nuclide is constructed. Alternatively, a combination therapy can be achieved by administering the chemotherapy and radioimmunotherapy agents in separate steps.

Another advantage of administering the prodrug-polymer in a later step, after the nuclide has been delivered as part of a previously given targetable construct, is that the synergistic effects of radiation and drug therapy can be manipulated and, therefore, maximized. It is hypothesized that tumors become more 'leaky' after RAIT due to radiation damage. This can allow a polymer-prodrug to enter a tumor more completely and deeply. This results in improved chemotherapy.

Multivalent Target Binding Proteins

It should also be noted that the disclosed conjugates and methods also contemplate multivalent target binding proteins which have at least three different target binding sites as described in Patent Appl. Ser. No. 60/220,782. Multivalent target binding proteins have been made by cross-linking several Fab-like fragments via chemical linkers. See U.S. Pat. Nos. 5,262,524; 5,091,542 and Landsdorp et al., *Euro. J. Immunol.* 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al., *Protein Engineering* 10(4): 423433 (1997).

Clearing Agents

A clearing agent may be used which is given between doses of the bsAb and the targetable construct. It has been discovered that a clearing agent of novel mechanistic action may be used with the disclosed diagnostic/therapeutic methods, namely a glycosylated anti-idiotypic Fab' fragment targeted against the disease targeting arm(s) of the bsAb. Anti-CEA (MN-14 Ab)×anti-peptide bsAb is given and allowed to accrete in disease targets to its maximum extent. To clear residual bsAb, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the therapeutic or diagnostic agent which is associated with the targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety.

Administration

The targetable construct and/or antibody may be administered intravenously, intraarterially, intraoperatively, endoscopically, intraperitoneally, intramuscularly, subcutaneously, intrapleurally, intrathecally, by perfusion through a regional catheter, or by direct intralesional injection, and can be by continuous infusion or by single or multiple boluses. or through other methods known to those skilled in the art for diagnosing (detecting) and treating diseased tissue. Further, the targetable construct may include agents for other methods of detecting and treating diseased tissue including, without limitation, conjugating dextran or liposome formulations to the targetable construct for use with ultrasound, or other contrast agents for use with other imaging modalities, such as X-ray, CT, PET, SPECT and ultrasound, as previously described.

Antibody Production

Antibodies and/or bi-specific antibodies, useful in the disclosed labeling and diagnostic/therapeutic methods, may be created by numerous standard methods as outlined below. The antibody or bi-specific antibody may comprise a monoclonal antibody or a fragment of a monoclonal antibody. Further, the antibody and/or bi-specific antibody may comprise an animal, human, chimeric or humanized antibody or a fragment of an animal, human, chimeric or humanized antibody. The arms of the antibody may be the same or different.

Abs to peptide backbones and/or haptens are generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

The antibodies used in the disclosed methods may be specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744. See also U.S. Pat. No. 5,965,132, to Thorpe et al., U.S. Pat. No. 6,004,554, to Thorpe et al., U.S. Pat. No. 6,071,491, to Epstein et al., U.S. Pat. No. 6,017,514, to Epstein et al., U.S. Pat. No. 5,882,626, to Epstein et al., U.S. Pat. No. 5,019,368, to Epstein et al., and U.S. Pat. No. 6,342,221, to Thorpe et al., all of which are incorporated herein by reference.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as disclosed in U.S. Pat. Nos. 4,361, 644 and 4,444,744, incorporated herein by reference. Markers of tumor vasculature (e.g., VEGF, PIGF), of tumor necrosis (Epstein patents), of membrane receptors (e.g., folate receptor, EGFR), of transmembrane antigens (e.g., PSMA), and of oncogene products (e.g. BCL-2, p53) can also serve as suitable tumor-associated targets for antibodies or antibody fragments. Markers of normal cell constituents which are expressed copiously on tumor cells, such as B-cell receptor antigens (e.g., CD19, CD20, CD21, CD22, CD23, and HLA-DR on B-cell malignancies), as well as cytokines expressed by certain tumor cells (e.g., IL-2 receptor in T-cell malignancies and IL-6 in multiple myeloma and diverse carcinomas) are also suitable targets for the antibodies and antibody fragments of the disclosed conjugates and methods. Antigens present on indolent forms of B-cell lymphomas, aggressive forms of B-cell lymphomas, chronic leukemias, multiple myeloma, and acute lymphatic leukemias may be selected. Antigens associated with non-Hodgkins lymphoma may be selected as well. Other well-known tumor associated antigens that can be targeted by the antibodies and antibody fragments of the disclosed conjugates and methods include, but are not limited to, CEA, CSAp, TAG-72, MUC-1, MUC-2, MUC-3, MUC-4, EGP-1, EGP-2, BrE3-antigen, PAM4-antigen, KC4, A3, KS-1, PSMA, PSA, tenascin, fibronectin, T101, S100, MAGE, HLA-DR, CD19, CD20, CD22, CD23, CD30, and CD74.

Another marker of interest is transmembrane activator and CAML-interactor (TACI). See Yu et al. *Nat. Immunol.* 1:252-256 (2000). Briefly, TACI is a marker for B-cell malignancies (e.g., lymphoma). Further it is known that TACI and B-cell maturation antigen (BCMA) are bound by the tumor necrosis factor homolog a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized Mabs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

Alternatively, fully human antibodies can be obtained from transgenic non-human animals. See, e.g., Mendez et al., *Nature Genetics*, 15: 146-156 (1997); U.S. Pat. No. 5,633, 425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics*, 16:133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., *Nat. Biotechnol.*, 14: 309-314 (1996). An scFv library with a large repertoire can be constructed by isolating V-genes from non-immunized human donors using PCR primers corresponding to all known $V_H$, $V_\kappa$ and $V_\lambda$ gene families. Following amplification, the $V_\kappa$ and $V_\lambda$ pools are combined to form one pool. These fragments are ligated into a phagemid vector. The scFv linker, $(Gly_4, Ser)_3$ (SEQ ID NO: 4), is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. Pastoris*. See, e.g., Ridder et al., *Biotechnology*, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J. Cancer*, 78: 181-188 (1998); Osbourn et al., *Immunotechnology*, 2: 181-196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

The bsAbs can be prepared by techniques known in the art, for example, an anti-CEA tumor Ab and an anti-peptide Ab are both separately digested with pepsin to their respective $F(ab')_2$s. The anti-CEA-Ab-$F(ab')_2$ is reduced with cysteine to generate Fab' monomeric units which are further reacted with the cross-linker bis(maleimido) hexane to produce Fab'-maleimide moieties. The anti-peptide Ab-$F(ab')_2$ is reduced with cysteine and the purified, recovered anti-peptide Fab'-SH reacted with the anti-CEA-Fab'-maleimide to generate the Fab'×Fab' bi-specific Ab. Alternatively, the anti-peptide Fab'-SH fragment may be coupled with the anti-CEA $F(ab')_2$ to generate a $F(ab')_2$×Fab' construct, or with anti-CEA IgG to generate an IgG×Fab' bi-specific construct. In one claim, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce bi-specific antibodies and antibody fragments. For example, bi-specific antibodies and antibody fragments can be produced in the milk of transgenic livestock. See, e.g., Colman, A., *Biochem. Soc. Symp.*, 63:141-147,1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bsAbs include engineered recombinant Abs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. *Natl. Acad. Sci.*, 92: 7021-7025, 1995. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ linker (SEQ ID NO: 4), and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into Chinese hamster ovary cells. Bi-specific fusion proteins are prepared in a similar manner. Bi-specific single-chain antibodies and bi-specific fusion proteins are included within the scope of the disclosed conjugates and methods.

Bi-specific fusion proteins linking two or more different single-chain antibodies or antibody fragments are produced in similar manner.

Recombinant methods can be used to produce a variety of fusion proteins. For example a fusion protein comprising a Fab fragment derived from a humanized monoclonal anti-CEA antibody and a scFv derived from a murine anti-diDTPA can be produced. A flexible linker, such as GGGS (SEQ ID NO: 5) connects the scFv to the constant region of the heavy chain of the anti-CEA antibody. Alternatively, the scFv can be connected to the constant region of the light chain of hMN- 14. Appropriate linker sequences necessary for the in-frame connection of the heavy chain Fd to the scFv are introduced into the $V_L$ and $V_K$ domains through PCR reactions. The DNA fragment encoding the scFv is then ligated into a staging vector containing a DNA sequence encoding the $C_H1$ domain. The resulting scFv-$C_H1$ construct is excised and ligated into a vector containing a DNA sequence encoding the $V_H$ region of an anti-CEA antibody. The resulting vector can be used to transfect mammalian cells for the expression of the bi-specific fusion protein.

Large quantities of bscAb and fusion proteins can be produced using *Escherichia coli* expression systems. See, e.g., Zhenping et al., *Biotechnology*, 14: 192-196, 1996. A functional bscAb can be produced by the coexpression in *E. coli* of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the *E. coli* alkaline phosphatase promoter which is inducible by phosphate starvation. Alternatively, single-chain fusion constructs have successfully been expressed in *E. coli* using the lac promoter and a medium consisting of 2% glycine and 1% Triton X-100. See, e.g., Yang et al., *Appl. Environ. Microbiol.*, 64: 2869-2874,1998. An *E. coli*, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., *Staphylococcal* protein A chromatography.

Functional bscAb and fusion proteins also can be produced in the milk of transgenic livestock. See, e.g., Colman, A., *Biochem. Soc. Symp.*, 63:141-147, 1998; U.S. Pat. No. 5,827,690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.*, 13: 1090-1093,1995; Fiedler et al., *Immunotechnology*, 3: 205-216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic recticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods*, 212: 149-160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.*, 42: 177 (1988); Bei et al., *J. Immunol. Methods*, 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods*, 212:149-160 (1998). The bscAb fragment, obtained as described above, is cloned into an expression vector containing the Drosphila metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

Preferred bi-specific antibodies of the disclosed conjugates and methods are those which incorporate the Fv of MAb Mu-9 and the Fv of MAb 679 or the Fv of MAb MN-14 and the Fv of MAb 679, and their animal, human, chimerized or humanized counterparts. The MN-14, as well as its chimerized and humanized counterparts, are disclosed in U.S. Pat. No. 5,874,540, incorporated herein by reference. Also preferred are bi-specific antibodies which incorporate one or more of the CDRs of Mu-9, MN-14, and/or 679. The antibody can also be a fusion protein or a bi-specific antibody that incorporates a Class-III anti-CEA antibody and the Fv of 679. Class-III antibodies, including Class-III anti-CEA are discussed in detail in U.S. Pat. No. 4,818,709, incorporated herein by reference.

The disclosed method encompasses the use of the bsAb and a therapeutic or diagnostic agent associated with the targetable construct discussed above in intraoperative, intravascular, and endoscopic tumor and lesion detection, biopsy and therapy as described in U.S. Pat. No. 6,096,289.

Conjugate Kit

The conjugate may be incorporated into a kit useful for diagnosing or treating diseased tissue in a subject, wherein the conjugate includes a diagnostic or therapeutic agent. For example, the conjugate may be labeled with F-18. The conjugate may function as a targetable molecule with at least one recognizable epitope. The kit may also include an antibody or an antibody fragment, (e.g., a conjugate as described herein which comprises an antibody, bi-specific antibody, and/or fragment). Optionally, the kit may include a clearing composition useful for clearing non-localized antibodies and antibody fragments, during the diagnostic or therapeutic method.

In Vitro Use of the Conjugate

The disclosed conjugates can be employed not only for therapeutic or imaging purposes, but also as aids in performing research in vitro. For example, the disclosed bsAbs and/or targetable constructs, labeled by the method disclosed herein, can be used in vitro to ascertain if a targetable construct can form a stable complex with one or more bsAbs. Such an assay would aid the skilled artisan in identifying targetable constructs which form stable complexes with bsAbs. This would, in turn, allow the skilled artisan to identify targetable constructs which are likely to be superior as therapeutic and/or imaging agents.

The assay is advantageously performed by combining the targetable construct in question with at least two molar equivalents of a bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96-well plate. To each well, is added solutions of targetable construct(s). Following incubation and analysis, one can readily determine which construct(s) bind(s) best to which bsAb(s).

It should be understood that the order of addition of the bsAb to the targetable construct is not crucial; that is, the bsAb may be added to the construct and vice versa. Likewise, neither the bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, ESMS, MALDI, high-field NMR or other appropriate method in conjunction with, or in place of, size-exclusion HPLC.

EXAMPLES

The present conjugates and methods are further illustrated by, though in no way limited to, the following examples. Further examples of the following synthesis reactions can be found in Organic Syntheses Collective Volume III, Editor E. C. Horning Copyright 1965 by John Wiley & Sons, Inc. New York, London; and Organic Syntheses Collective Volume V, Editor Henry Baumgarten, Copyright 1973 by John Wiley & Sons, Inc. New York, London, Sydney, Toronto.

A wide variety of second molecules (i.e., carriers or targeting molecules) are suitable for the described methods and may be utilized in the Examples described herein, provided that the second molecule can be linked to the fluorinated carbohydrate molecule. In the peptides described herein, HSG and DTPA may be interchanged. Where the second molecule is a targeting construct that includes a radionuclide and the targeting construct is to be used in diagnostic methods, it may be desirable that the targeting construct have a particular level of specific activity (e.g., a specific activity of 800-1000 Ci/mmol may be desirable).

Example 1

Conjugate Prepared by Linking FDG via a Hydrazone/Hydrazine Linkage

FIG. 1 displays the reaction of 2-Fluoro-2-Deoxy-D-Glucose with $H_2N$—NH—$C_6H_4$—CO-Lys(HSG)-Tyr-Lys(HSG)-$NH_2$ (IMP 278) to form a hydrazone linkage.

Figure 3:
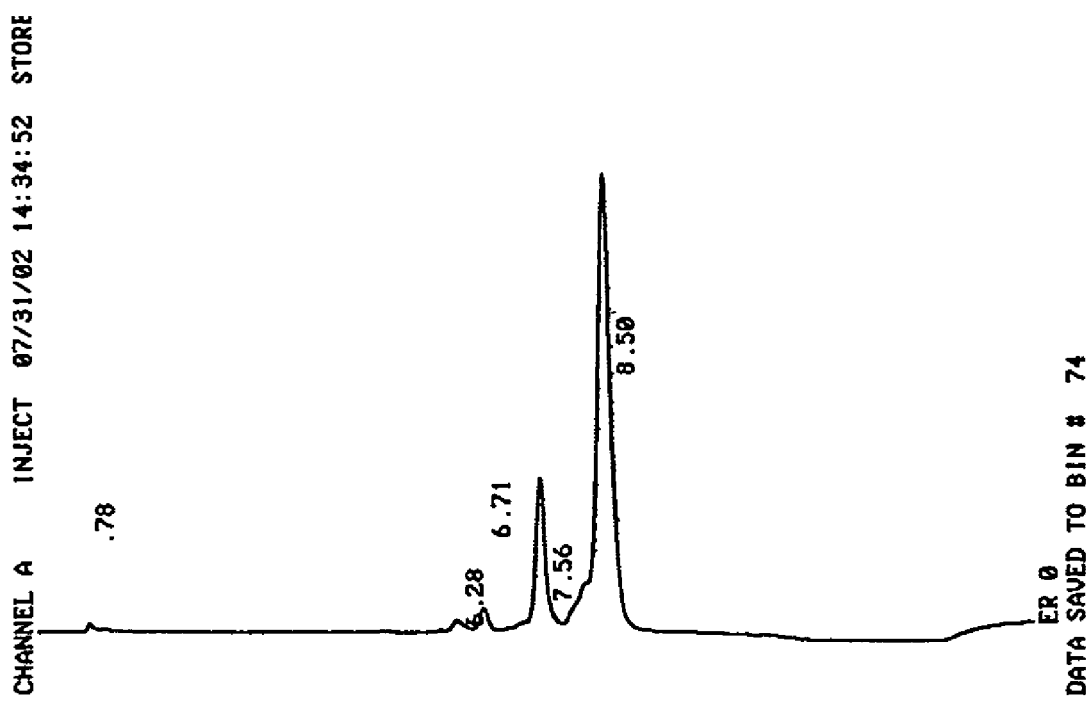
FIG. 3 is a graphic representation of an HPLC analysis of IMP 278 reacted with "cold" FDG at 30 minutes post-reaction.
Figure 4:
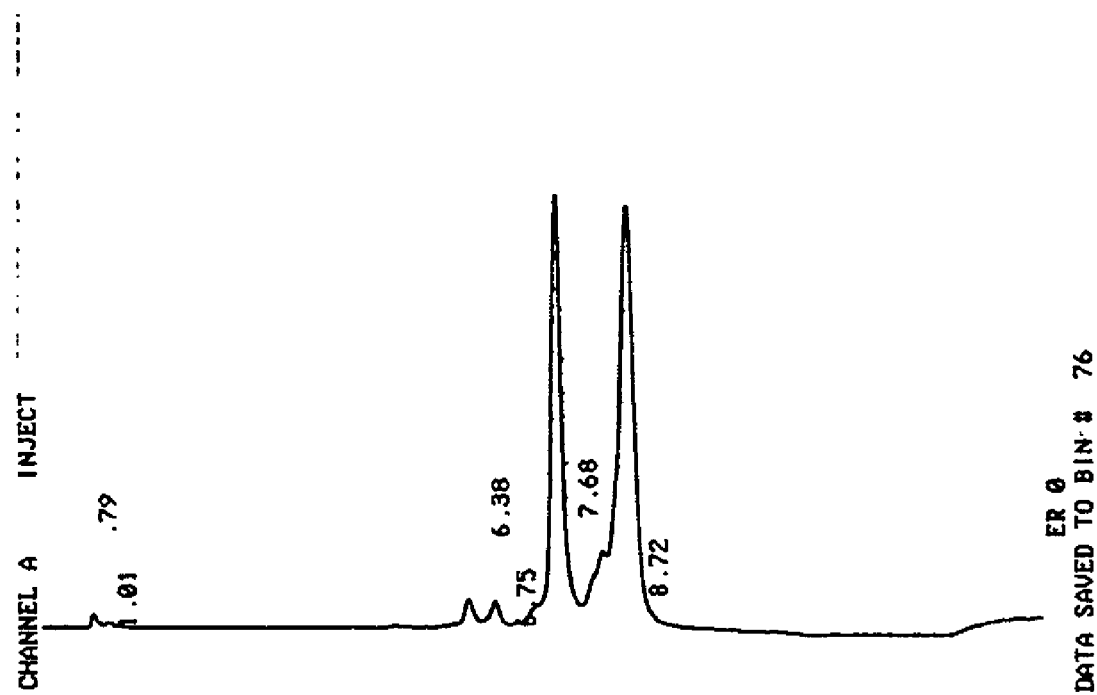
FIG. 4 is a graphic representation of an HPLC analysis of IMP 278 reacted with "cold" FDG at 1 hour and 40 minutes post-reaction.
Figure 5:
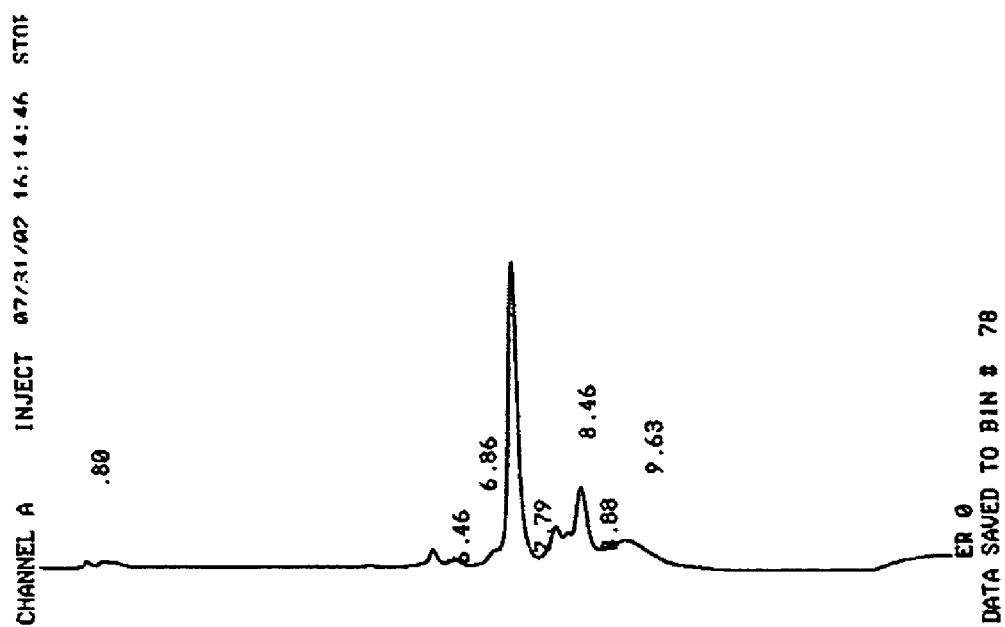
FIG. 5 is a graphic representation of an HPLC analysis of the reaction material from FIG. 4, after incubation at 50° C. for 20 minutes.

The peptide, 0.0209 g ($1.95 \times 10^{-5}$ mol, IMP 278) was dissolved in 0.5 ml water and 0.0039 g ($2.14 \times 10^{-5}$ mol, 110 mol %, FDG) was added. The buffer, 0.1 ml (pH 6 citrate, 0.1 M) was then added. The reaction was incubated at room temperature and monitored by HPLC. See FIGS. 2-5. HPLC analysis at 1 hr and 40 min showed that the reaction was about 40% complete. See FIG. 3. The reaction was heated in a 50° C. water bath for about 20 min and analyzed by HPLC, which showed that the reaction was mostly complete. See FIG. 4. HPLC was then used to obtain the newly formed peptide IMP 279 (i.e., the conjugate). The peptide had the expected mass of MH+1237 by electospray mass spectroscopy.

Other suitable peptides for forming a conjugate with FDG by a hydrazone/hydrazine bond include N $H_2$—NH—$CH_2$—CO-Lys(DTPA)-Tyr-Lys(DTPA)—$NH_2$ (IMP 209), $NH_2$—NH—$C_6H_4$—CO-Lys(DTPA)-Tyr-Lys(DTPA)-$NH_2$ (IMP 221), $NH_2$—NH—$C_6H_4$—CO-D-Lys(HSG)-D-Glu-D-Lys(HSG)-$NH_2$ (IMP 280), and $NH_2$—NH—$C_6H_4$—CO-D-Lys(HSG)-D-Ala-D-Lys(HSG)-$NH_2$ (IMP 283).

Figure 6:
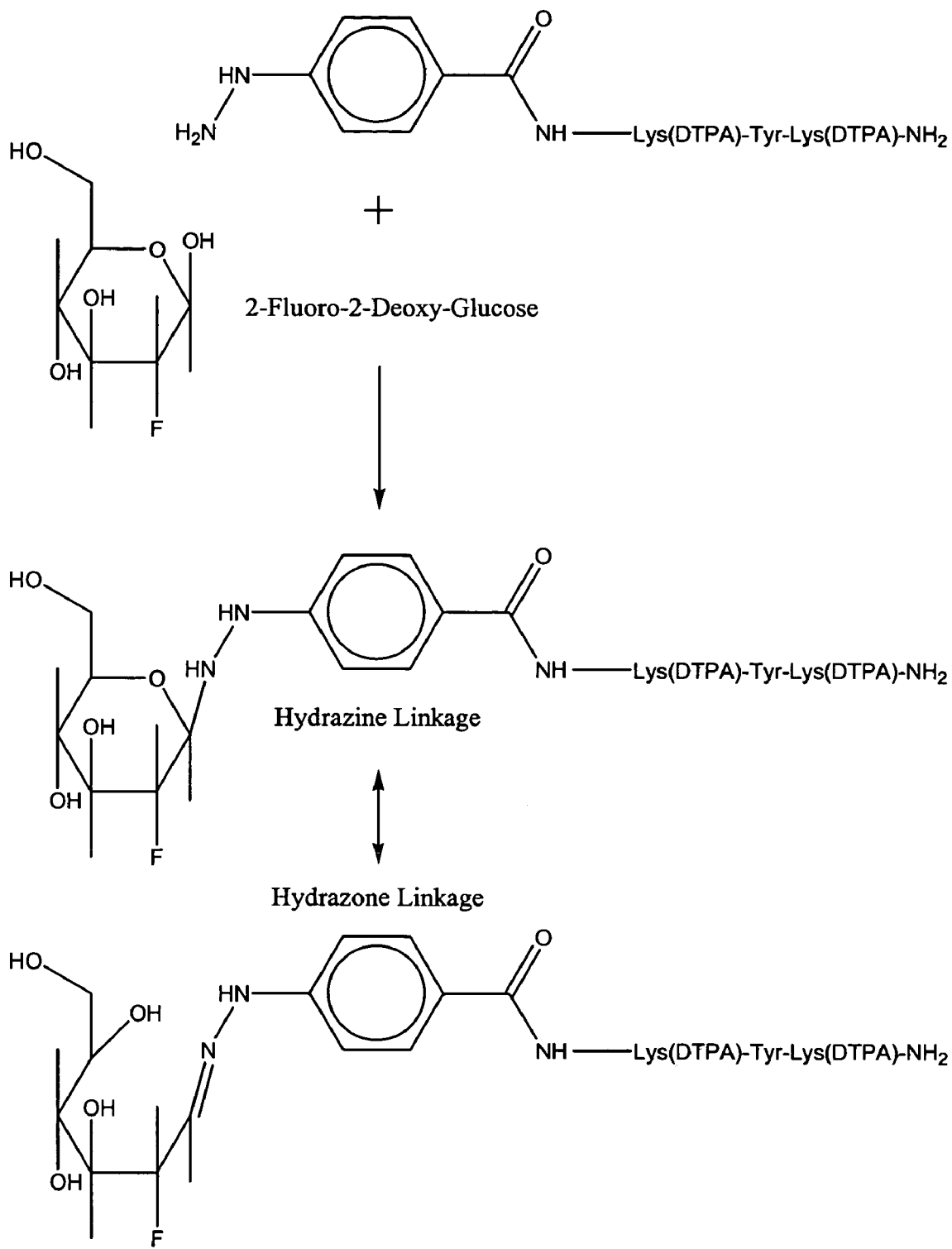
FIG. 6 is a schematic representation of the reaction of FDG with $NH_2$—NH—$C_6H_4$—CO-Lys(DTPA)-Tyr-Lys(DTPA)-$NH_2$ (IMP 221).

Similar to IMP 278, the hydrazine peptide IMP 221, (or IMP 209, IMP 280, IMP 283) can react with FDG as outlined in FIG. 6. In FIG. 6, the terminal nitrogen atom of the hydrazine group of a carrier molecule can function as a nucleophile that may attack the carbonyl carbon of FDG, (i.e., at C1). The stability of this conjugation can be probed by making a non-radioactive or "cold" FDG peptide that includes a metal chelator (FDG is available from Sigma, St. Louis, Mo.). The peptide then can be labeled with In-111 to allow monitoring of in-vivo and in-vitro stability. If desirable, the hydrazone linkage can be stabilized by reducing the bond with borohydride to form a hydrazine linkage.

Example 2

Conjugate Prepared by Linking FDG via an Amino/Imino or Amido Linkage

The FDG is reacted with a nitrogen derivative such as an amine, or a hydrazine derivative to form an adduct. The peptide is dissolved in an aqueous solution at pH 5-7 and mixed with the FDG adduct. Sodium cyanoborohydride (or sodium borohydride) is then added and the reaction is allowed to proceed at room temperature for 15 min before it is quenched with acetic acid and the conjugated peptide is purified.

The FDG molecule (or carrier) may be modified to promote formation of particular bonds or linkages. For example, it may be desirable to treat FDG with a nitrogen-containing molecule to create an aminated derivative of FDG (e.g., by reacting with an aminooxy, a hydrazide, and/or a thiosemicarbazide group). The nitrogen atoms within the aminated derivatives can function in nucleophilic attacks at carbonyl carbons of carriers or target molecules, such as peptides, proteins, and antibodies. In particular, FDG can be aminated and reacted with a peptide to form an amide, amine, or imino bond or linkage. Reductive amination can be used to form a more stable link. For example, an aminated derivative of FDG can be reacted with carbonyl-containing peptides such as O=CH—CO-Lys(X)-Tyr-Lys(X)—NH2 (IMP 213). Alternatively, an amino-containing peptide such as Gly-Lys (DTPA)-Tyr-Lys(DTPA)-NH2 (IMP 223) (SEQ ID NO: 2) can be reacted with FDG to form a stable bond by reductive amination.

In another claim, hydroxlamines (or aminooxy containing molecules) can be reacted with either FDG or a carrier molecule to create an oxime. The nitrogen atom of the oxime can then function in a nucleophilic attack at a carbonyl carbon on either the FDG or the carrier molecule to form an amide, amine, or imine bond or linkage. Creation of aminooxy-functionalized carbohydrates has been described. See Rodriguez et al., *J. Org. Chem.* 1998, 63, 7134-7135.

Example 3

Synthesis of IMP 286: $H_2N-NH-CS-NH-C_6H_4-CO$-D-Lys(HSG)-D-Glu-D-Lys(HSG)-$NH_2$ $MH^+$ 1097 (Thiosemicarbazide-Containing Peptide)

Figure 7:
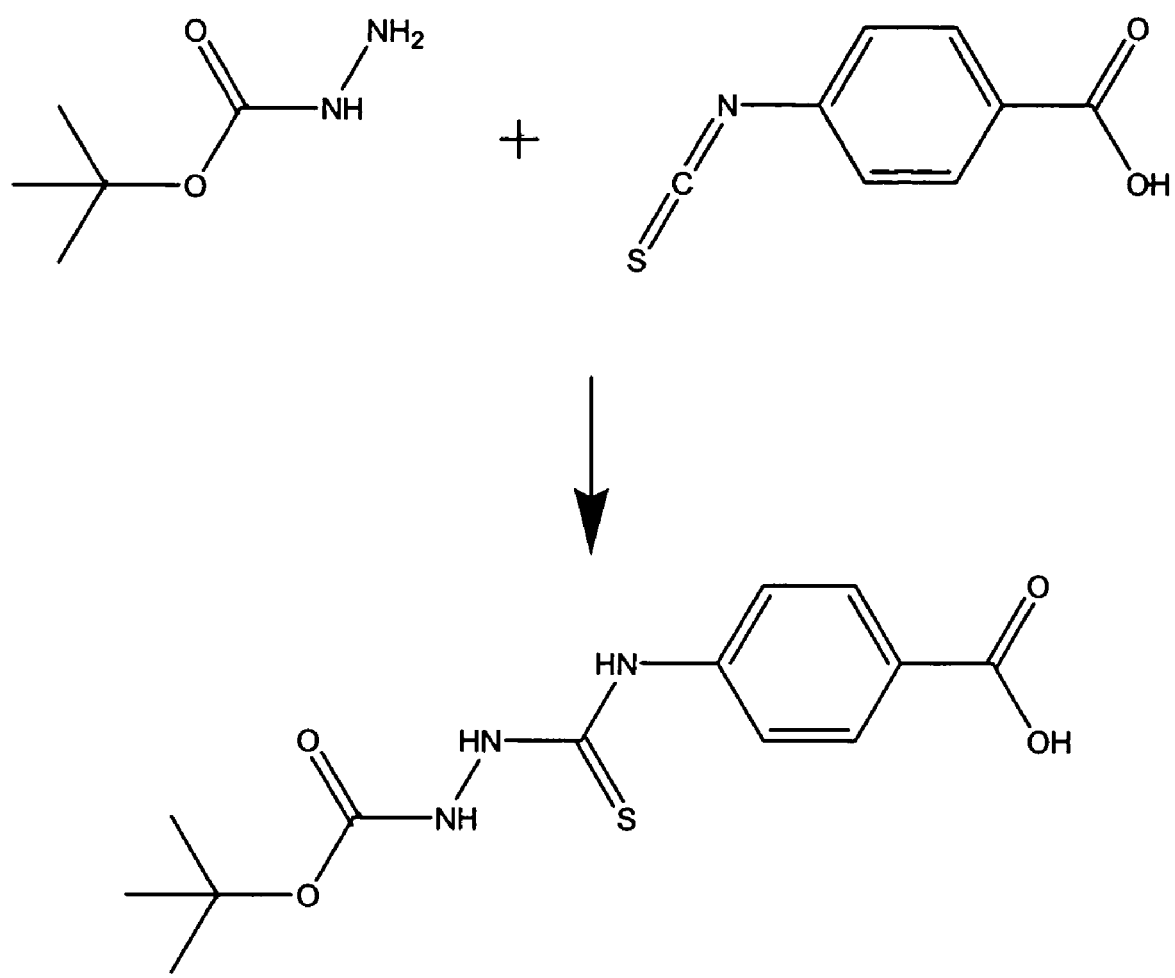
FIG. 7 is a schematic representation of the synthesis of a peptide precursor with a thiosemicarbazide linker.

FIG. 7 shows a schematic representation of the synthesis of a precursor having a thiosemicarbazide linker. A thiosemicarbazide-containing peptide, (IMP 286), was synthesized as follows.

Rink amide resin, 2.026 g (0.6 mmol/g) was suspended in 40 mL N-methylpyrrolidinone (NMP) for 30 min with $N_2$ purge mixing to swell the resin. The Fmoc on the resin was removed with two 50 mL washes with 25% piperidine in NMP. The first piperidine cleavage wash was mixed with the resin for 4 min and the second piperidine cleavage wash mixed with the resin for 17 minutes. The resin was washed with NMP and isopropanol (IPA) using 40 mL portions in the following order NMP, IPA, NMP, IPA, 4×NMP. The first amino acid, Aloc-D-Lys(Fmoc)-OH, 3.327 g, 7.35×10$^{-3}$ mol was mixed with 1.222 g N-hydroxybenzotriazole monohydrate (HOBt), 1.2 mL 1,3-diisopropylcarbodiimide (DIC), and 28 mL NMP. This solution was $N_2$ purge mixed with the resin for 17 hr at room temperature. The resin was washed with NPM and IPA. The Fmoc was cleaved from the side chain of the lysine with 25% piperidine in NMP as described above. The resin was washed with NMP and IPA. The Trt-HSG-OH, 3.228 g was mixed with 1.209 g HOBt, 1.0 mL DIC, 22 mL NMP, 2.2 mL N,N-diisopropylethylamine (DIEA), and 1.0 mL DIC. The trityl-HSG-OH solution was mixed with the resin for 20 hr and then washed with NMP and IPA. A ninhydrin test, to check for the presence of unreacted amines, was negative. The resin was washed with 3×40 mL portions of dichloromethane. The resin was split into two, roughly equal, portions. Half of the original resin was used in the subsequent reactions. Acetic acid, 1 mL was mixed with 2 mL piperidine and dissolved in 40 mL dichloromethane. Tetrakis(triphenylphosphine)palladium(0), 0.2291 g, was dissolved in the dichloromethane solution. Tributyltinhydride, 5 mL, was added to the resin. The palladium solution was then added to the resin and the solution was $N_2$ purge mixed for 1 hr. The Aloc cleavage was repeated with a second lot of palladium and tributyltin hydride for another hour. The resin was washed with 2×40 mL dichloromethane, NMP, IPA, 2×25% piperidine in NMP, NMP, IPA, NMP, IPA, and 4×NMP. The next amino acid, Fmoc-D-Glu(OBut)-OH, 1.575 g (3.7×10$^{-3}$ mol) was mixed with 0.572 9 HOBt and 0.6 mL DIC in 14 mL NMP. The solution was added to the resin and mixed for 18 hr. The resin was washed with the usual washes of NMP and IPA. The resin was ninhydrin negative. The Fmoc group on the glutamic acid residue was then cleaved with piperidine, and the resin was washed with NMP and IPA as described. The second Aloc-D-Lys(Fmoc)-OH was added followed by the addition of Trityl-HSG-OH to the side chain of the lysine as described above. The α-Aloc of the lysine was removed and the Boc-NH—NH—CS—NH—$C_6H_4CO_2H$, 2.08 g (6.69×10$^{-3}$ mol) was coupled to the resin as described for the other amino acid couplings. The peptide was cleaved from the resin with 20 mL TFA containing 0.5 mL anisole and 0.5 mL triisopropyl silane. The peptide was cleaved for 3 hr and precipitated in ether. The peptide was purified by HPLC to afford 0.1105 g of the desired peptide ESMS $MH^+$ 1097.

Example 4

Conjugate Prepared by Linking FDG via a Thiosemicarbazone Linkage

Figure 8:
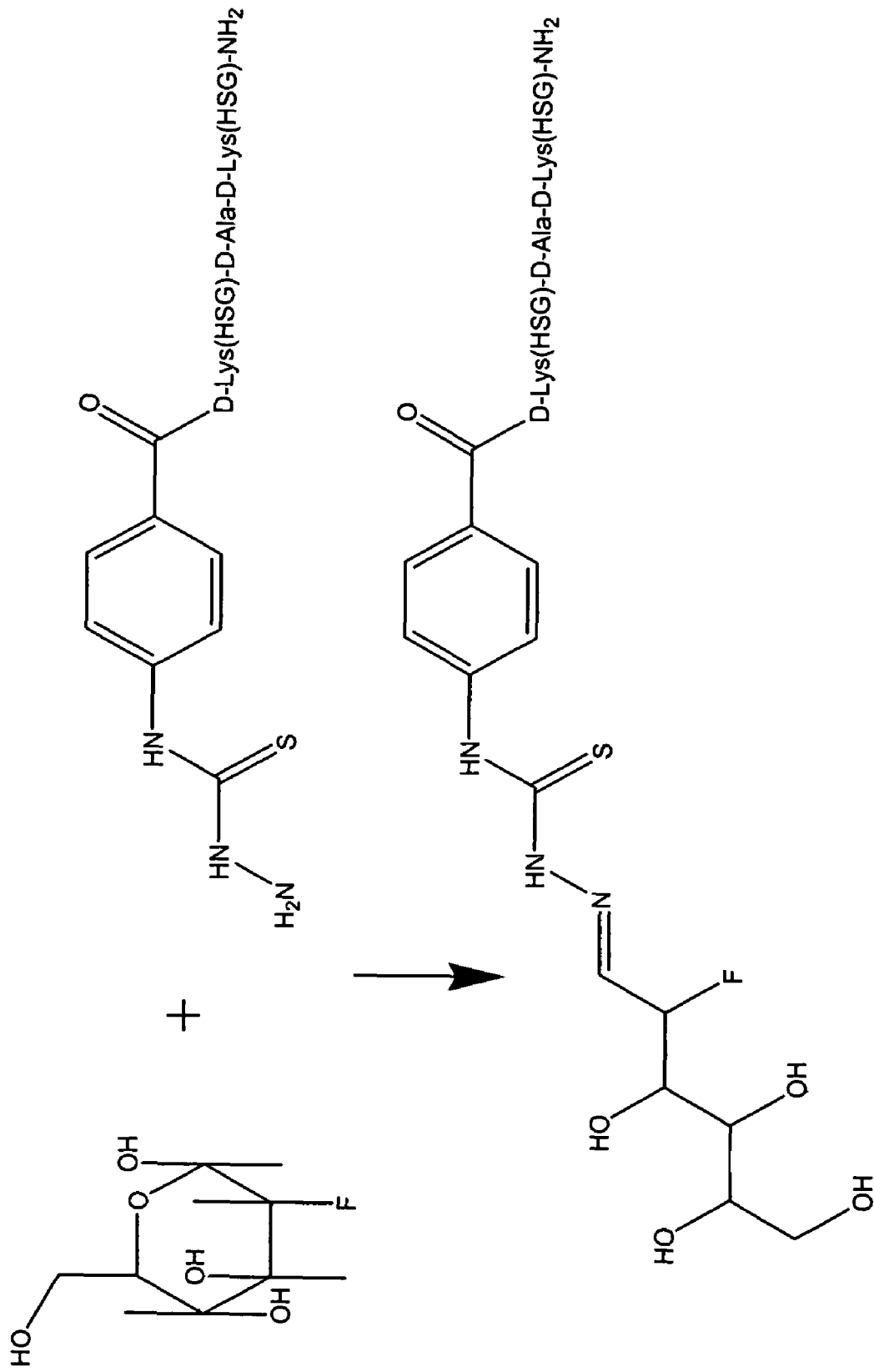
FIG. 8 is a schematic representation of the reaction of FDG with a peptide containing a thiosemicarbazide linker.

FIG. 8 shows the schematic representation of a conjugate formed by the reaction of a thiosemicarbazide-containing peptide with FDG to form a thiosemicarbazone linkage. The thiosemicarbazide-containing peptide of Example 3 was used to synthesize a conjugate as follows.

IMP 287 Synthesis (FDG-Peptide Conjugate with a Thiosemicarbazone Linkage)

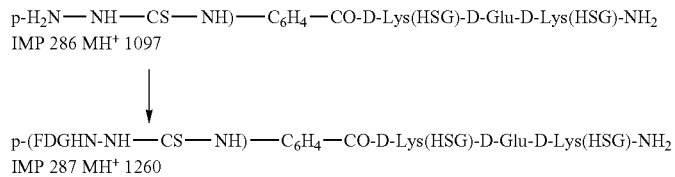

p-$H_2N$—NH—CS—NH)—$C_6H_4$—CO-D-Lys(HSG)-D-Glu-D-Lys(HSG)-$NH_2$
IMP 286 $MH^+$ 1097

↓ p-(FDGHN-NH—CS—NH)—$C_6H_4$—CO-D-Lys(HSG)-D-Glu-D-Lys(HSG)-$NH_2$
IMP 287 $MH^+$ 1260

The peptide, IMP 286, 0.0204 g (1.86×10$^{-5}$ mol) was mixed with 0.0038 g (2.09×10$^{-5}$ mol) of FDG and dissolved in a solution of 0.5 mL water and 0.1 mL of 0.1 M citrate buffer pH 5.96. The reaction was allowed to stand at room temperature overnight. Acetic acid 50 μL was added in two portions over four hours. The peptide FDG conjugate was diluted in water and purified by HPLC to obtain 0.0065 g (28% yield) of the desired product after lyophilization.

Example 5

Synthesis of an FDG-Peptide Conjugate by an Ylide Intermediate

FIG. 9 shows a schematic representation of the formation of an FDG-peptide conjugate by a nitrogen-ylide intermediate.

Example 6

Synthesis of a Peptide with a Boronic Acid Linker

Figure 10:
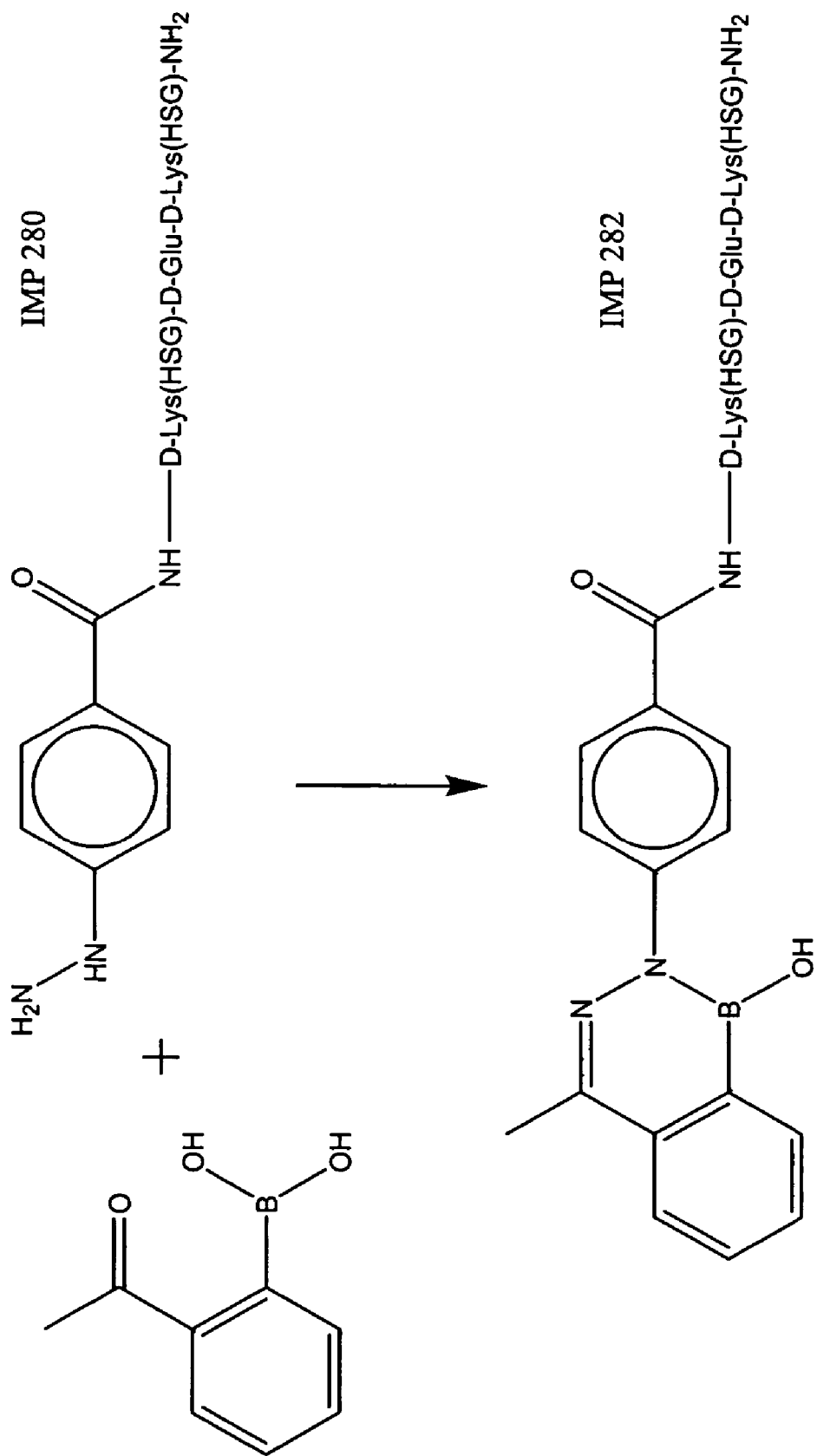
FIG. 10 is a schematic representation of the reaction of a boronic acid-containing molecule with $NH_2$—NH—$C_6H_4$—CO—NH-D-Lys(HSG)-D-Glu-D-Lys(HSG)-$NH_2$ (IMP 280).

FIG. 10 shows the synthesis of a peptide containing a boronic acid linker (IMP 282), which is formed by reacting NH$_2$—NH—C$_6$H$_4$—CO—NH-D-Lys(HSG)-D-Glu-D-Lys (HSG)-NH$_2$ (IMP 280) with a boronic acid molecule (2-acetylphenyl boronic acid).

The peptide, IMP 280: NH$_2$—NH—C$_6$H$_4$—CO—NH-D-Lys(HSG)-D-Glu-D-Lys(HSG)-NH$_2$ (0.0312 g), was mixed with 0.0194 g of 2-acetylboronic acid and dissolved in 0.6 mL of 0.1 M pH 6.0 citrate buffer. The solution was incubated at room temperature for 2 hr and then purified by HPLC to afford 0.0213 g of purified conjugate. (ESMS MH$^+$ 1166.)

Example 7

Synthesis and Purification of F-18, 2-Fluoro-2-Deoxy-D-Glucose

Figure 11:
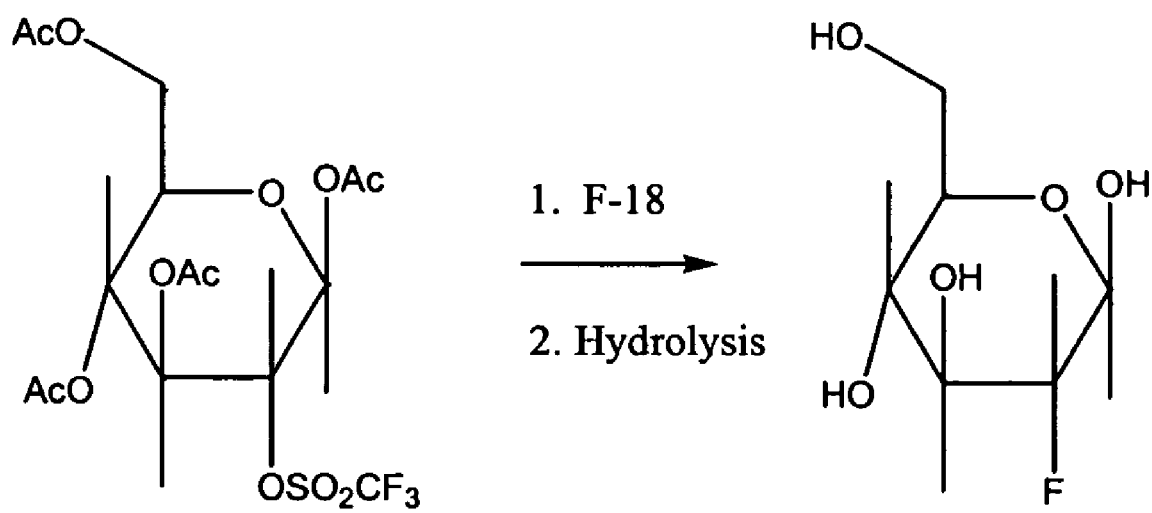
FIG. 11 is a schematic representation of the synthesis of FDG by hydrolysis of an acetylated precursor, (1,3,4,6,-tetra-O-Acetyl-2-O-trifluoromethanesulfonyl-β-D-mannopyranose).

FIG. 11 shows the synthesis of F-18, 2-Fluoro-2-Deoxy-D-Glucose from 1,3,4,6-tetra-O-Acetyl-2-O-trifluoromethanesulfonyl-β-D-mannopyranose (e.g., by reacting F-18 and hydrolyzing with sodium methoxide). Synthesis of FDG and other fluorinated sugars has been described. See Beuthien-Baumann et al., *Carbohydrate Res.* 2000, 327, 107-118; EP 0 167 103. 1,3,4,6-tetra-O-acetyl-2-O-trifluoromethanesulfonyl-β-D-mannose (20 mg), dissolved in 1 mL of anhydrous acetonitrile can be reacted with dried F-18 (Eastern Isotopes) in the presence of Kryptofix 222 and potassium carbonate at reflux temperature for 5 min.

Figure 12:
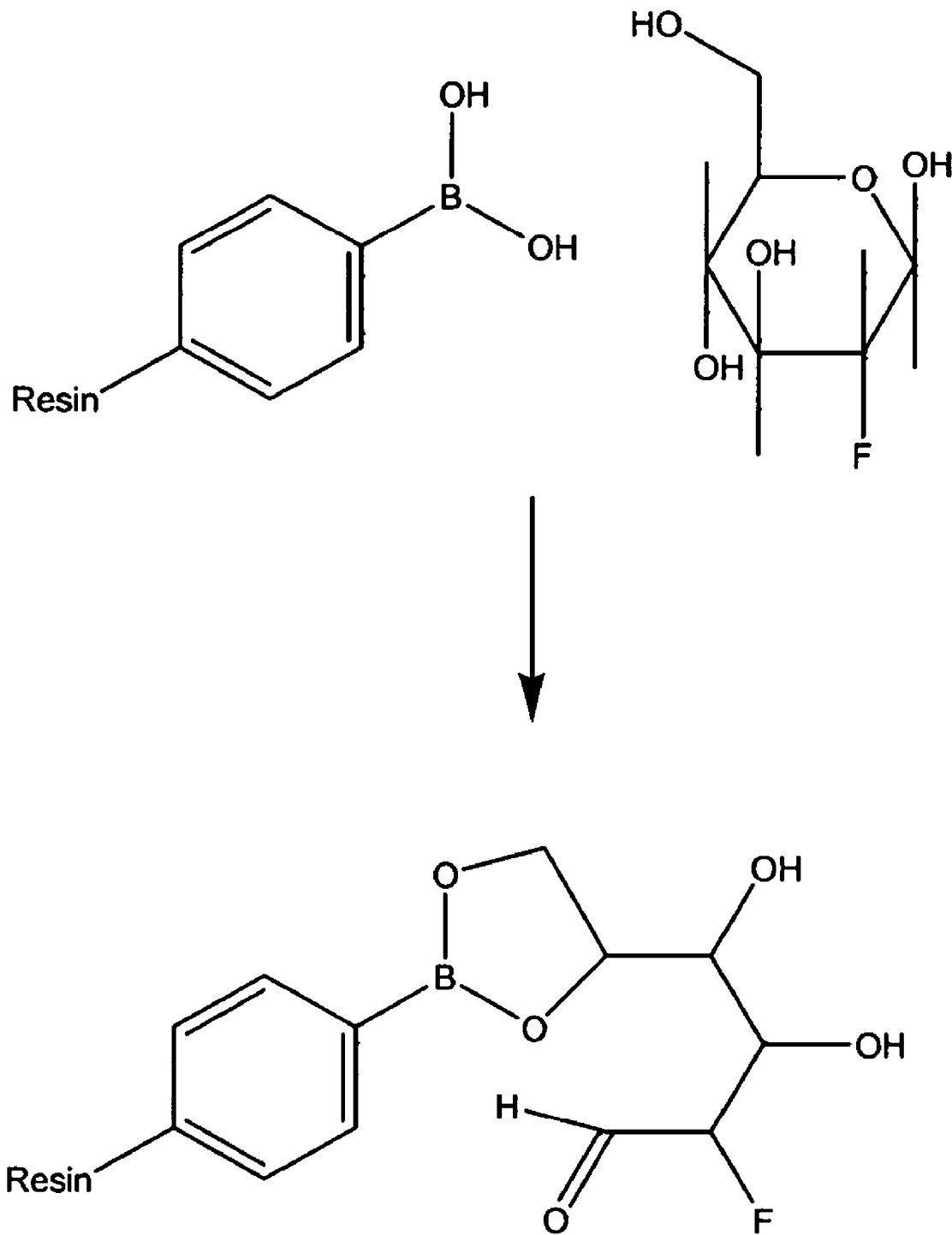
FIG. 12 is a schematic representation of the reaction of FDG with a boronic acid resin.

After the FDG has been synthesized, it can be purified by passing the FDG through a boronic acid resin column. FIG. 12 shows FDG binding to a boronic acid resin. Boronic acid derivatives are known to bind glucose and other carbohydrates at pH 8.5 and release them at pH 4. As shown by the results in Table 1, boronic acid resins can be used to selectively purify FDG from a FDG/glucose mixture, based on preferential binding of FDG.

| Sample | Before Resin | After Resin |
|---|---|---|
| Glucose | 0.53 g/L | 0.23 g/L |
| FDG | 0.24 g/L | 0.06 g/L |

Glucose (0.0141 g) was dissolved in a solution containing 25 mL of saline and 3 mL of 1 M NaHCO$_3$. The solution (10 mL) was mixed with 1 mL of the Boronic acid immobilized resin (Pierce 20244) and incubated with mixing in a 15 mL centrifuge tube at room temperature for 50 min. The solution was decanted and the glucose concentration was measured with a commercial glucose sensor.

The cold 2-fluoro-2-deoxy-D-glucose, 0.0161 g was dissolved in a solution containing 28 mL of saline and 3.4 mL of 1 M NaHCO$_3$. The FDG solution was treated in the same manner as the glucose solution.

Figure 13:
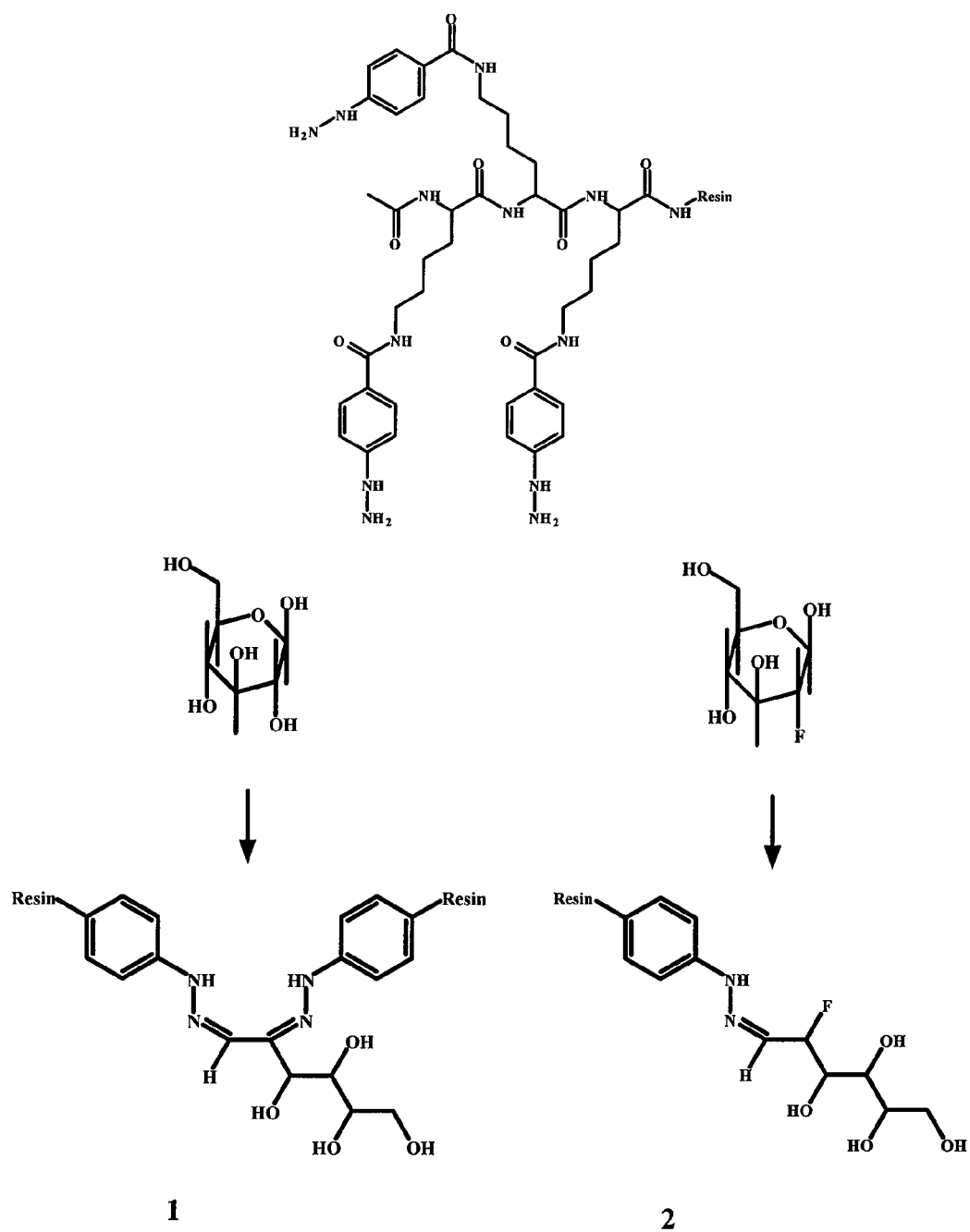
FIG. 13 is a schematic representation of the reaction between glucose and FDG with a phenyl hydrazine resin.
Figure 14:
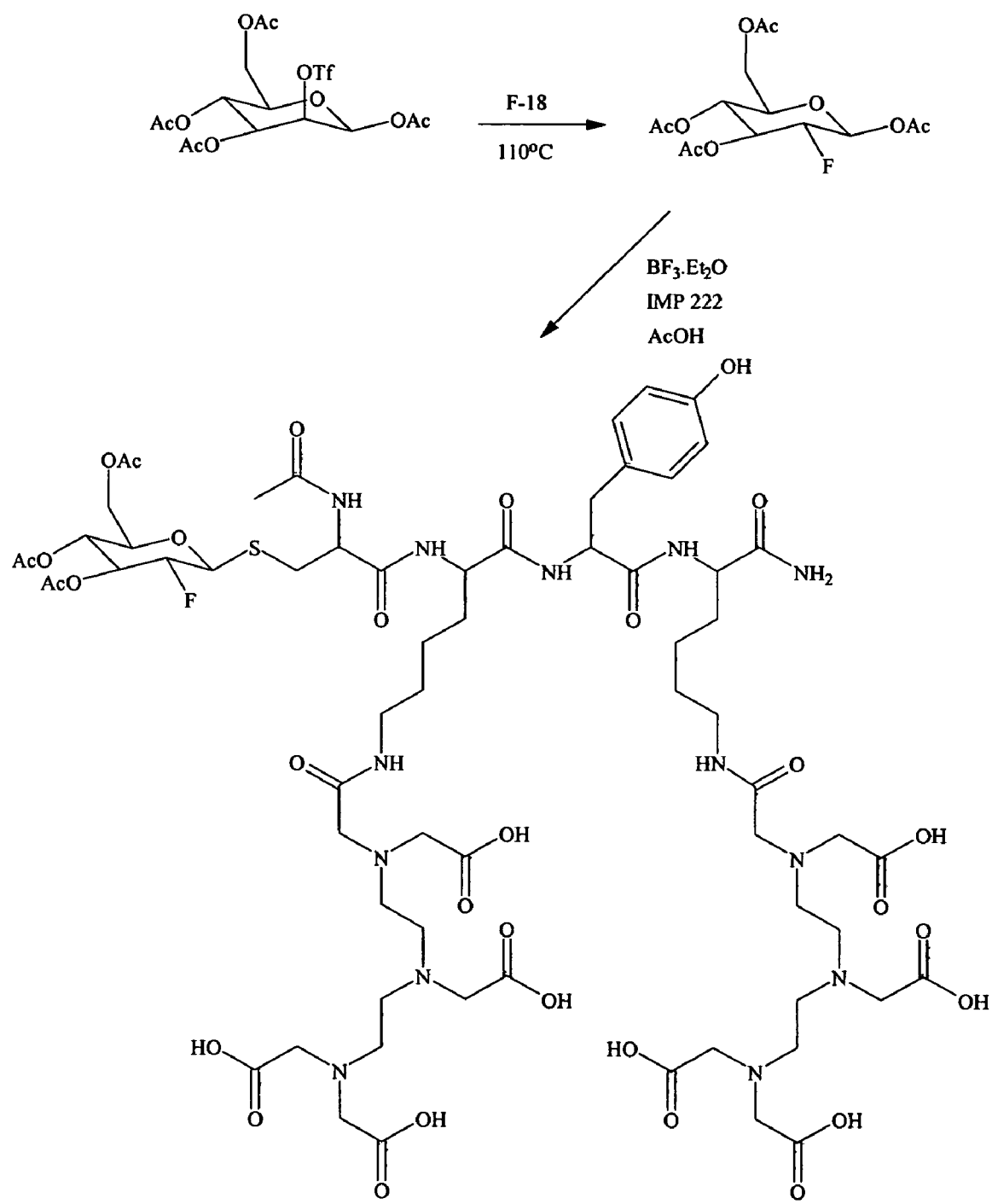
FIG. 14 is a schematic representation of the synthesis of an F-18, FDG-IMP 222 conjugate.
Figure 15:
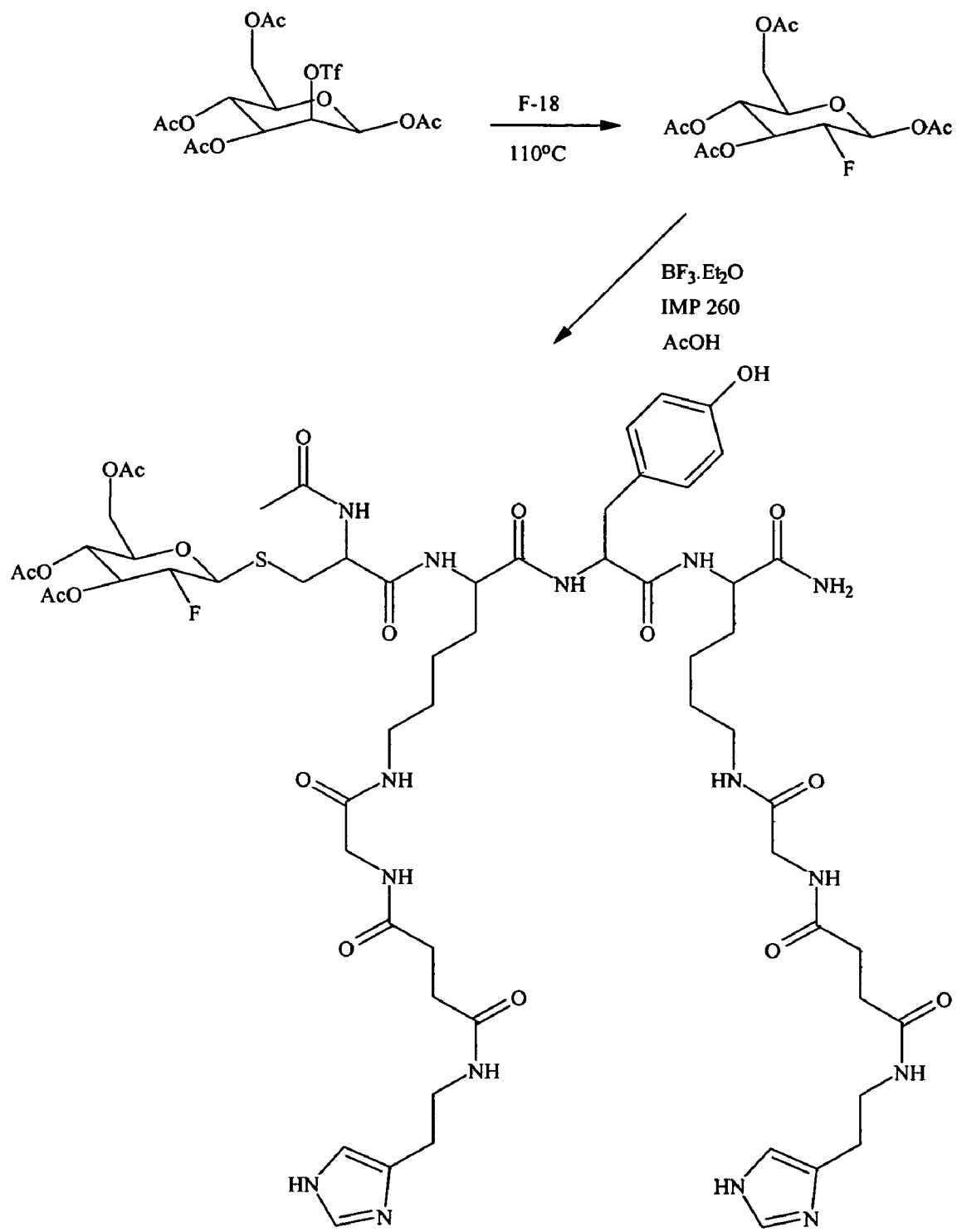
FIG. 15 is a schematic representation of the synthesis of an F-18, FDG-IMP 286 conjugate formed by treating the F-18 labeled tetra-acetyl sugar with $BF_3$ etherate.

Alternatively, the FDG may be purified by passing the FDG through a phenyl hydrazine resin column. See FIG. 13. For example, sugars can bind the phenyl hydrazine at a pH of approximately 5-8, and the sugar is released from the resin at only a more acidic pH of approximately 2.

The phenyl hydrazine resin can form an osazone bond with glucose (bonded at the C1 and C2 positions), while the resin can only form a hydrazone bond with FDG (bonded at the C1 position). As such, the FDG can be released from the phenyl hydrazine column under less stringent acidic conditions.

The FDG precursor, 1,3,4,6-tetra-O-Acetyl-2-O-[$^{18}$F]-β-D-glucose may also be separated or purified by contacting a reaction mixture with a resin capable of being alkylated such as an activated thiol-, amino-, or hydrazino-containing resin.

Activated thiol-containing resins are commercially available (e.g., see Amersham Biosciences), or alternatively, a thiol-containing resin (e.g., see Novabiochem) can be activated by treating the resin with a mild base that deprotonates the thiol group. The activated resin can be used to purify 1,3,4,6-tetra-O-Acetyl-2-O-[$^{18}$F]-β-D-glucose from a mixture of 1,3,4,6-tetra-O-Acetyl-2-O-[$^{18}$F]-β-D-glucose and 1,3,4,6-tetra-O-Acetyl-2-O-trifluoromethanesulfonyl-β-D-mannopyranose, based on their different reactivities for the activated thiol resin. The mannose trifluoromethanesulfonyl (triflate) will bind covalently (to form a sulfide bond) to the resin when the thiol-containing resin displaces the triflate group. The fluorinated carbohydrate will not react with the thiol-containing resin, so it should not form a covalent bond to the resin. As such, the specific activity of the solution can be increased by passing the solution through a column that contains the resin; binding the 1,3,4,6-tetra-O-Acetyl-2-O-[$^{18}$F]-β-D-glucose and 1,3,4,6-tetra-O-Acetyl-2-O-trifluoromethanesulfonyl-β-D-mannopyranose; and washing and eluting the 1,3,4,6-tetra-O-Acetyl-2-O-[$^{18}$F]-β-D-glucose to obtain a solution with an increased concentration of F-18-labeled glucose and a higher specific activity. This separation might also be achieved by silical gel chromatography or reverse phase HPLC.

Unreacted F-18 can be separated from the labeled product with a sep-pak. The F-18 will be washed off with 0.1 M HCL, while the tetraacetyl carbohydrate will stick to the C-18 material. The product can then be eluted with a suitable solvent such as CH$_2$Cl$_2$, THF, or ethanol, and the solvent evaporated. The acetyl groups are then hydrolyzed with base as described in the literature. The solution is then neutralized and concentrated. The F-18, FDG may then be reacted with any suitable peptide (e.g., a thiosemicarbazide peptide such as IMP 286).

Example 8

Conjugate Prepared by Linking FDG via a Sulfide, Amino, Imino, or Amido Linkage

Further halogenated derivatives of FDG may be created to provide good leaving groups for a nucleophilic attack by a sulfur atom of a thiol group. For example, a derivative of FDG containing a chlorine substitution at the C1 position may be useful for a reaction with Ac-Cys-Lys(DTPA)-Tyr-Lys (DTPA)-NH$_2$ (IMP 222) (SEQ ID NO: 1), which contains a free thiol group. For example, 3,4,6-tri-O-acetyl-1-Chloro-2-Fluoro-2-Deoxy-D-Glucose may be mixed with the IMP 222 at pH 5-9, and the mixture stirred at room temperature until the reaction with FDG is complete.

To create a further halogenated derivative of FDG, a hydroxyl group at the 1 position on an FDG molecule or derivative can be selectively replaced by a halogen such as Cl or Br. For example, the FDG precursor can be treated, as described by Patt et al., *Appl. Radiat. Isot.* 2002, 57, 705-712. The C1 halogen can then be displaced by a sulfur atom of a thiol group, (e.g., the thiol group of IMP 222), to form a stable sulfide bond or linkage to a carrier or targeting peptide. (e.g., see Zhu et al., *J. Org. Chem.* 2003, 68, 5641-51, incorporated herein by reference in its entirety). Alternatively, the C1 halogen can be displaced by a nitrogen atom (e.g., within an amino group present on a carrier or targeting peptide).

The C1 acetyl ester can also be activated by treating with BF$_3$ etherate, and the activated acetal ester can be linked to a nucleophile such as a thiol group (e.g., within a thiophenol or a cysteine residue in a peptide or protein). For example, F-18 labeled tetra-acetyl glucose can be prepared as described in Example 7. The labeled tetra-acetyl glucose is then reacted with a thiol-containing peptide dissolved in glacial acetic acid. $BF_3$ etherate is then added to the reaction mixture. When the reaction is complete (as monitored by reverse phase HPLC using a scintillation detector), the mixture is diluted with water, placed on a sep-pak, and washed with water. The reaction is then eluted with ethanol. The acetyl groups can be hydrolyzed with a mild base (0.33 M NaOH).

Example 9

Labeling with $^{111}$In

The $^{111}$In (~300 µCi/kit) was diluted to 0.5 mL in deionized water and added to the lyophilized kits. The kits were heated in a boiling water bath for 15 min, the vials were cooled and 0.5 mL of $2.56\times10^{-5}$ M In in 0.5 M acetate buffer was added and the kits were again heated in the boiling water bath for 15 min. The labeled peptide vials were cooled to room temperature and evaluated by reverse phase HPLC (HPLC conditions: Waters Nova-Pak C-18, 8×100 mm RCM column eluted at 3 mL/min with a linear gradient from 100% (0.1% TFA in $H_2O$) to 100% (90% $CH_3CN$, 0.1% TFA, 10% $H_2O$)). The HPLC analysis revealed that the minimum concentration of peptide needed for labeling (4.7% loose $^{111}$In), with this formulation, was 35 µg/mL. The reverse phase HPLC trace showed a sharp $^{111}$In labeled peptide peak. The labeled peptide was completely bound when mixed with excess 679 IgG by size exclusion HPLC.

Example 10

Generation of an Anti-Peptide Ab

Immunocompetent mice are injected with a mixture of the peptide antigen in complete Freund's adjuvant. Two booster shots of the peptide mixed with incomplete Freund's adjuvant are administered over the next several weeks. Spleen cells are harvested from the animals and fused with Sp2/0-Ag14 myeloma cells. Culture supernatants of the resulting clones are analyzed for anti-peptide reactivity by ELISA, using plates coated with the original peptide immunogen. Enzyme-deficient hybridomas are isolated to enable selection of fused cell lines, and selected clones grown in culture media to produce the anti-peptide Abs.

Example 11

Purification of Anti-Peptide Ab

Anti-peptide Ab is purified chromatographically using a protein A column to isolate the IgG fraction, followed by ion-exchange columns to clean the desired product. The Ab of interest is finally purified by using an affinity column comprised of the peptide of interest bound to a solid support, prepared by chemically coupling said peptide to activated beads or resin.

Example 12

Digestion of Anti-Peptide Ab to F(ab')$_2$

The anti-peptide Ab is incubated with 200 µg/µL of pepsin at pH 4 for one hour and purified by a tandem column of protein A, to remove undigested IgG, followed by G-50-Sephadex, to remove low molecular weight contaminants.

Example 13

Reduction of Anti-Peptide-Ab to Fab'-SH

The anti-peptide-F(ab')$_2$ is reduced to a Fab' fragment by reaction with a freshly prepared cysteine solution in 0.1M PBS, containing 10 mM EDTA. The progress of the reaction is followed by HPLC, and when complete, in about 1 h, the Fab'-SH is purified by spin-column chromatography and stored in deoxygenated buffer at pH <5 containing 10 mM EDTA.

Example 14

Preparation of Anti-CEA-IgGx Anti-Peptide-Fab' Bi-Specific Ab

The IgG-hydrazide-maleimide from Example 10 is treated with an equimolar amount of anti-peptide Fab'-SH, at pH 6.0, for 30 minutes at room temperature. Remaining free thiol groups are blocked by a 30-minute reaction with iodoacetamide. The bi-specific Ab anti-CEA-IgG×anti-peptide-Fab' is purified by size-exclusion chromatography to remove unreacted Fab', followed by affinity chromatography using solid-phase-bound peptide to separate IgG×Fab' from unreacted IgG.

Example 15

Conjugation of a Carboxylesterase to di-DTPA-Peptide

Carboxylesterase (5 mg) in 0.2 M phosphate buffer, pH 8.0, is treated with a five-fold molar excess of the cross-linking agent sulfo-succinimidyl-[4-maleimidomethyl]-cyclohexane-1-carboxylate (sulfo-SMCC). After stirring two hours at room temperature, the activated enzyme is separated from low molecular weight contaminants using a spin-column of G-25 Sephadex and equilibrated in 0.1 M phosphate buffer, pH 7, containing 1 mM EDTA. The peptide to be labeled (ten-fold molar excess) is added to the activated enzyme and dissolved in the same buffer as used in the spin-column. After stirring for one hour at room temperature, the peptide carboxylesterase conjugate is purified from unreacted peptide by spin-column chromatography on G-25 Sephadex in 0.25 M acetate buffer, pH 6.0. Successful conjugation is demonstrated by indium-111 labeling of an aliquot of the conjugate, and analysis by size-exclusion HPLC.

All patents and other references cited in the specification are indicative of the level of skill of those skilled in the art to which the invention pertains. Further, all patents and other references are hereby incorporated by reference in their entireties, including any tables and figures, to the same extent as if each reference had been or has been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred claims are exemplary and are not intended as limitations on the scope of the invention. Changes therein and other uses will occur to those skilled in the art, which are encompassed within the invention.

It will be readily apparent to one skilled in the art that varying substitutions and modifications may be made to the invention disclosed herein without departing from the scope and spirit of the invention. For example, a variety of different binding pairs can be utilized, as well as a variety of different therapeutic and diagnostic agents. Thus, such additional claims are within the scope of the present invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred claims and optional features, modification and variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for claims, additional claims are described by taking any 2 different values as the endpoints of a range. Such ranges are also within the scope of the described invention.

What is claimed Is:

1. A conjugate comprising a 2-Fluoro-2-Deoxy-D-Glucose (FDG) linked to a peptide through at least one of a hydrazone linkage, a thiosemicarbazone linkage, a boronic acid linkage, or a sulfide linkage wherein the 2-Fluoro-2-Deoxy-D-Glucose comprises F-18 and wherein the protein or peptide is selected from the group consisting of IMP 209, IMP 213, IMP 221, IMP 222, IMP 223, IMP 260, IMP 278, IMP 280, IMP 282, IMP 283 and IMP 286.

* * * * *

```
                              SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Lys Tyr Lys
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Lys Tyr Lys
  1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Tyr Lys Lys Cys
  1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide
```

-continued

```
<400> SEQUENCE: 4

Gly Gly Gly Gly Ser Gly Gly Gly Gly Ser Gly Gly Gly Gly Ser
 1               5                  10                  15

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 5

Gly Gly Gly Ser
 1
```